(12) United States Patent
Hall et al.

(10) Patent No.: US 11,273,206 B2
(45) Date of Patent: Mar. 15, 2022

(54) TARGETING OF PHARMACEUTICAL AGENTS TO PATHOLOGIC AREAS USING BIFUNCTIONAL FUSION POLYPEPTIDES

(71) Applicant: Counterpoint Biomedica LLC, Santa Monica, CA (US)

(72) Inventors: Frederick L. Hall, Laguna Niguel, CA (US); Erlinda M. Gordon, Carmel, CA (US)

(73) Assignee: Counterpoint Biomedica LLC, Santa Monica, CA (US)

( * ) Notice: Subject to any disclaimer, the term of this patent is extended or adjusted under 35 U.S.C. 154(b) by 378 days.

(21) Appl. No.: 16/546,068

(22) Filed: Aug. 20, 2019

(65) Prior Publication Data

US 2019/0374617 A1    Dec. 12, 2019

Related U.S. Application Data

(62) Division of application No. 14/869,776, filed on Sep. 29, 2015, now Pat. No. 10,420,820.

(60) Provisional application No. 62/214,752, filed on Sep. 4, 2015, provisional application No. 62/103,489, filed on Jan. 14, 2015, provisional application No. 62/056,859, filed on Sep. 29, 2014.

(51) Int. Cl.
| | |
|---|---|
| *A61K 38/00* | (2006.01) |
| *A61K 38/38* | (2006.01) |
| *A61K 31/337* | (2006.01) |
| *A61K 31/713* | (2006.01) |
| *A61K 47/64* | (2017.01) |
| *A61K 38/17* | (2006.01) |
| *A61K 38/18* | (2006.01) |
| *A61K 38/20* | (2006.01) |
| *C07K 16/18* | (2006.01) |
| *C07K 16/22* | (2006.01) |

(52) U.S. Cl.
CPC .......... *A61K 38/385* (2013.01); *A61K 31/337* (2013.01); *A61K 31/713* (2013.01); *A61K 38/1754* (2013.01); *A61K 38/18* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/2053* (2013.01); *A61K 47/643* (2017.08); *C07K 16/18* (2013.01); *C07K 16/22* (2013.01); *C07K 2319/00* (2013.01)

(58) Field of Classification Search
CPC .................................................. A61K 38/385
USPC ....................................................... 530/350
See application file for complete search history.

(56) References Cited

U.S. PATENT DOCUMENTS

| | | | |
|---|---|---|---|
| 6,063,593 | A | 5/2000 | Gordon |
| 6,227,369 | B1 | 5/2001 | Glassman |
| 6,387,663 | B1 | 5/2002 | Hall et al. |
| 6,410,015 | B1 | 6/2002 | Gordon |
| 6,955,898 | B2 | 10/2005 | Hall |
| 7,459,541 | B2 | 12/2008 | Hall |
| 7,795,023 | B2 | 9/2010 | Hall |
| 2005/0048063 | A1 | 3/2005 | Ruoslahti |
| 2009/0093407 | A1 | 4/2009 | Hall et al. |
| 2010/0016413 | A1 | 1/2010 | Hall et al. |
| 2010/0196482 | A1 | 8/2010 | Radovic-Moreno et al. |
| 2014/0017331 | A1 | 1/2014 | McCarthy et al. |
| 2014/0088021 | A1 | 3/2014 | Riggs-Sauthier et al. |

FOREIGN PATENT DOCUMENTS

WO    WO 2005/117993    12/2005

OTHER PUBLICATIONS

Amos and Lowe, "How Taxol stabilises microtubule structure," Chem. & Biol., 6(3):R65-69, Mar. 1999.
Aoki el al., "Screening of paclitaxel-binding molecules from a library of random peptides displayed on T7 phage particles using paclitaxel-photoimmobilized resin." Bioconjugate Chem., 18(6):1981-1986, Nov.-Dec. 2007.
Bennet and Kim, "Polymer Nanoparticles for Smart Drug Delivery," Application of Nanotechnology in Drug Delivery, Chapter 8, pp. 257-310, 2014.
Bryckaert et al., "Of von Willebrand factor and platelets," Cell. Mol. Life Sci., 75(2):307-326, Jan. 2015.
Cruz et al., "Interaction of the von Willebrand Factor (vWF) with Collagen. Localization of the Primary Collagen-Binding Site By Analysis of Recombinant vWF A Domain Polypeptides ," J. Biol. Chem., 270:10822-10827, May 1995.
DeLano et al., "Convergent solutions to binding at a protein-protein interface," Science, 287(5456):1279-1283, Feb. 2000.
Du and O'Reilly, "Advances and challenges in smart and functional polymer vesicles," Royal Soc Chem, Soft Matter 5:3544-3561, Jun. 2009.

(Continued)

*Primary Examiner* — Sean E Aeder
(74) *Attorney, Agent, or Firm* — Fish & Richardson P.C.

(57) ABSTRACT

Provided herein are new compositions and methods to target pharmaceutical agents to pathological areas by utilizing bifunctional fusion polymers or nanoparticles. These fusion polymers and nanoparticles contain two or more domains: (i) sequences that bind to exposed collagenous (XC-) proteins present in pathological areas, including cancerous lesions and (ii) domains that bind to pharmaceutical agents. The drug-binding functionality of these fusion polymers and nanoparticles is based on high-affinity, non-covalent interactions.

18 Claims, 14 Drawing Sheets

Specification includes a Sequence Listing.

(56) References Cited

OTHER PUBLICATIONS

Fang and DeClerck, "Targeting the tumor microenvironment: from understanding pathways to effective clinical trials," Cancer Res., 73(16):4965-4977, Aug. 2013.
Fang et al., ""Loop" domain is necessary for taxol-induced mobility shift and phosphorylation of Bcl-2 as well as for inhibiting taxol-induced cytosolic accumulation of cytochrome c and apoptosis," Cancer Res., 58(15):3202-3208, Aug. 1998.
Fine et al., "Enhanced endothelial cell functions on rosette nanotube-coated titanium vascular stents," Int. Journal of Nanomedicine, 4:91-97, 2009.
Ginsburg and Bowie, "Molecular genetics of von Willebrand disease," Blood, 79(10):2507-2519, May 1992.
Gordon et al., "Capture and expansion of bone marrow-derived mesenchymal progenitor cells with a transforming growth factor-beta1-von Willebrand's factor fusion protein for retrovirus-mediated delivery of coagulation factor IX," Hum. Gene Ther., 8(11):1385-1394, Jul. 1997.
Gordon et al., "Inhibition of metastatic tumor growth in nude mice by portal vein infusions of matrix-targeted retroviral vectors bearing a cytocidal cyclin G1 construct," Cancer Res. 60(13):3343-3347, Jul. 2000.
Gordon et al., "Le Morte du Tumour: Histological features of tumor destruction in chemo-resistant cancers following intravenous infusions of pathotropic nanoparticles bearing therapeutic genes," Int J Oncol, 30(6):1297-1307, Jun. 2007.
Gordon et al., "Lesion-targeted injectable vectors for vascular restenosis," Hum Gene Ther., 12(10):1277-1287, Jul. 2001.
Gordon et al., "Pathotropic nanoparticles for cancer gene therapy, Rexin-GTM IV: Three-year clinical experience," Int J Oncol, 29(5):1053-1064, Nov. 2006.
Hall et al., "Design, expression, and renaturation of a lesion-targeted recombinant epidermal growth factor-von Willebrand factor fusion protein: efficacy in an animal model of experimental colitis," Intl J Mol Med., 6(6):635-643, Dec. 2000.
Hall et al., "Molecular engineering of matrix-targeted retroviral vectors incorporating a surveillance function inherent in von Willebrand factor," Hum Gene Ther., 11(7):983-993, May 2000.
Hall et al., "Pathotropic targeting advances clinical oncology: Tumor-targeted localization of therapeutic gene delivery ," Oncol Rep, 24(4):829-833, Oct. 2010.
Hoylaerts et al., "von Willebrand factor binds to native collagen VI primarily via its A1 domain," Biochem. J., 324(Pt 1):185-191, May 1997.
Hu et al., "Polymeric nanotherapeutics: clinical development and advances in stealth functionalization strategies," Nanoscale, 6(1):65-75, Jan. 2014.
International Search Report and Written Opinion issued in PCT/US2015/053035 dated Mar. 11, 2016 (18 pages).
Jhaveri and Torchilin, "Multifunctional polymeric micelles for delivery of drugs and siRNA," Front Pharmacol., 5(77):1-26, Apr. 2014.
Katzenellenbogen et al., "NFX1-123 and poly(A) binding proteins synergistically augment activation of telomerase in human papillomavirus type 16 E6-expressine cells." J. Virol., 81(8):3786-3796, Apr. 2007.
Kim et al., "Engineered Polymers for Advanced Drug Delivery," Eur J Pharm Biopharm., 71(3):420-430, Mar. 2009.
Kopecek et al., "Peptide-directed self-assembly of hydrogels," Acta Biomater., 5:1-19 (Oct. 2008) (Author Manuscript).
Kratz, "Albumin as a drug carrier: design of prodrugs, drug conjugates and nanoparticles," J. Controlled Release, 132(3):171-183, Dec. 2008.
Kwon et al., "Analysis on the current status of targeted drug delivery to tumors," J. Controlled Release, 164(2):108-114, Dec. 2012.
Lankhof et al., "A3 domain is essential for interaction of von Willebrand factor with collagen type III," Thromb Haemost, 75(6):950-958, Jun. 1996.
Liu et al., "Incorporation of tumor vasculature targeting motifs into moloney murine leukemia virus env escort proteins enhances retrovirus binding and transduction of human endothelial cells," J Virol, 74(11):5320-5328, Jun. 2000.
Mora-Huertas et al., "Polymer-based nanocapsules for drug delivery," Int J. Pharmaceutics, 385(1-2):113-142, Jan. 2010.
Park, "The optimal formulation variables for tumor targeting," J. Controlled Release, 157(3):315-316, Feb. 2012.
Rao et al., "3'-(p-azidobenzamido)taxol photolabels the N-terminal 31 amino acids of beta-tubulin," J. Biol. Chem., 269(5):3132-3134, Feb. 1994.
Rao et al., "Characterization of the taxol binding site on the microtubule. 2-(m-Azidobenzoyl)taxol photolabels a peptide (amino acids 217-231) of beta-tubulin," J. Biol. Chem., 270(35):20235-20238, Sep. 1995.
Rodi et al., "Screening of a library of phage-displayed peptides identifies human bcl-2 as a taxol-binding protein," J. Mol. Biol., 285(1): 197-203, Jan. 1999.
Rugo et al., "Randomized Phase III Trial of Paclitaxel Once Per Week Compared With Nanoparticle Albumin-Bound Nab-Paclitaxel Once Per Week or Ixabepilone With Bevacizumab as First-Line Chemotherapy for Locally Recurrent or Metastatic Breast Cancer: CALGB 40502/NCCTG N063H (Alliance)," J. Clinical Oncology, 33(21):2361-2369, Jul. 2015.
Sounni and Noel, "Targeting the tumor microenvironment for cancer therapy," Clinical Chem., 59(1):85-93, Jan. 2013.
Sutton et al., "Functionalized micellar systems for cancer targeted drug delivery," Pharm Res., 24(6):1029-1046, Jun. 2007.
Sznol et al., "Antagonist antibodies to PD-1 and B7-H1 (PD-L1) in tire treatment of advanced human cancer," Clinical Cancer Research, Oct. 1, 2013: 19(19):5542-5542.
Takagi et al., "Collagen-binding Domain within Bovine Propolypeptide of von Willebrand Factor," Journal of Biological Chemistry, 266(9):5575-5579, Mar. 1991.
Takagi, J., et al., "A collagen/gelatin-binding decapeptide derived from bovine propolypeptide of von Willebrand factor," Biochemistry 31(36):8530-8534, Sep. 1992.
Tuan et al., "Engineering, expression and renaturation of targeted TGF-beta fusion proteins," Connect Tissue Res., 34(1):1-9, 1996.
Waehler et al., "Engineering targeted viral vectors for gene therapy," Nature Reviews Genetics, 8(8):573-587, Aug. 2007.
Yang et al., "Binding site on human immunoglobulin G for the affinity ligand HWRGWV," Journal of Molecular Recognition: An Interdisciplinary Journal, May 2010; 23(3):271-282.
Yang et al., "Hexamer peptide affinity resins that bind the Fc region of human immunoglobulin G," J. Peptide Res., 66(s1): 120-137, Dec. 2005.
Yatuv et al., "Enhancement of the efficacy of therapeutic proteins by formulation with PEGylated liposomes: a case of FVIII, FVIIa and G-CSF," Expert opinion on drug delivery, Feb. 1, 2010; 7(2):187-201.

FIG. 6A
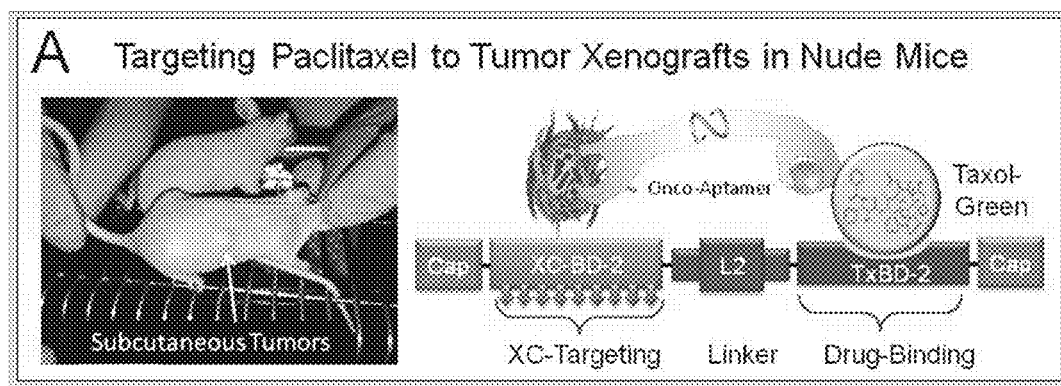
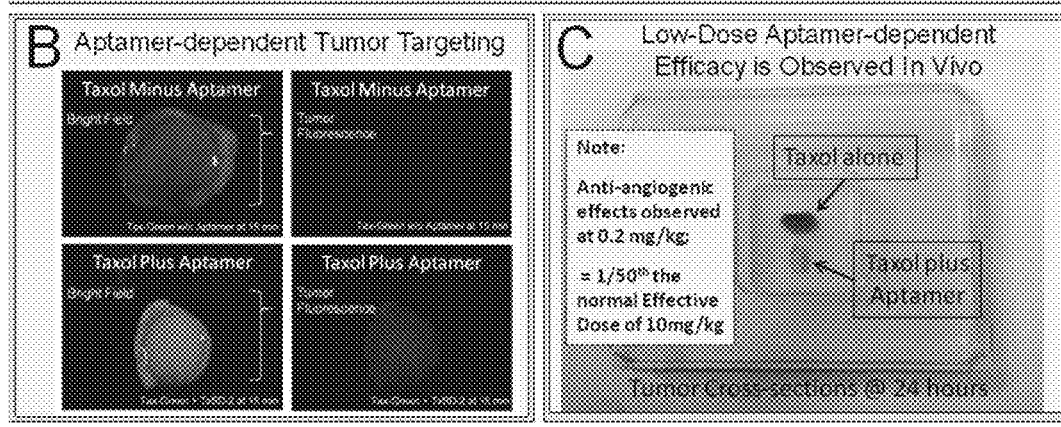
FIG. 6B          FIG. 6C

FIG. 8A
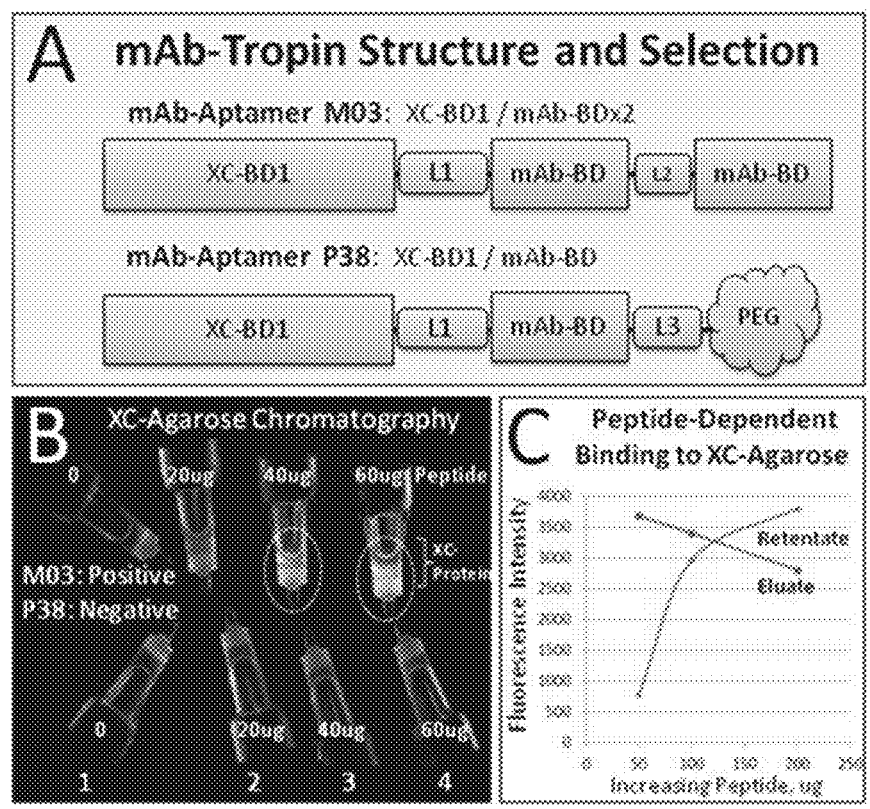
FIG. 8B
FIG. 8C
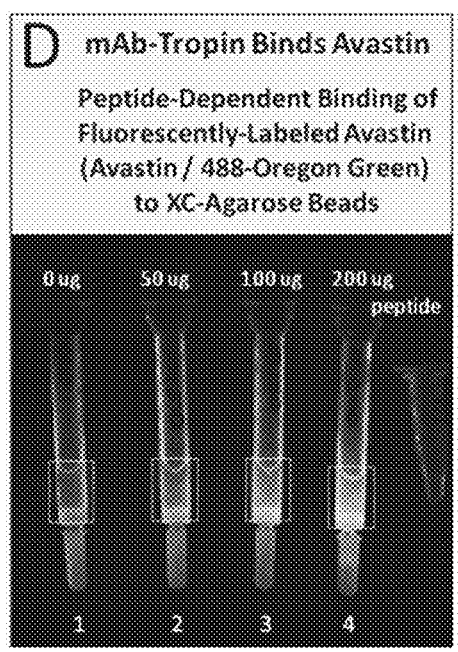
FIG. 8D

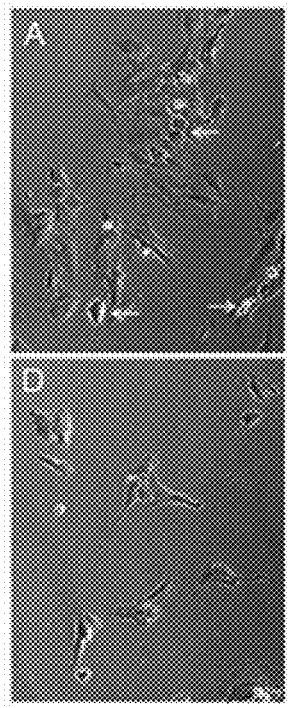 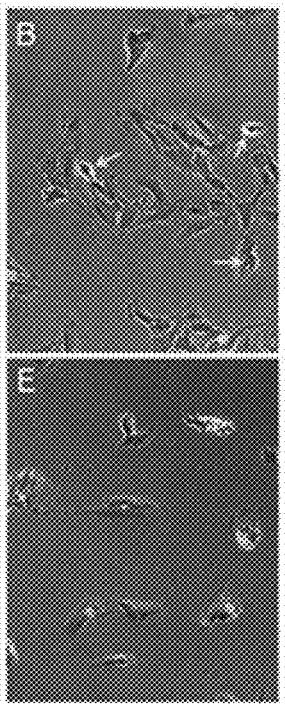 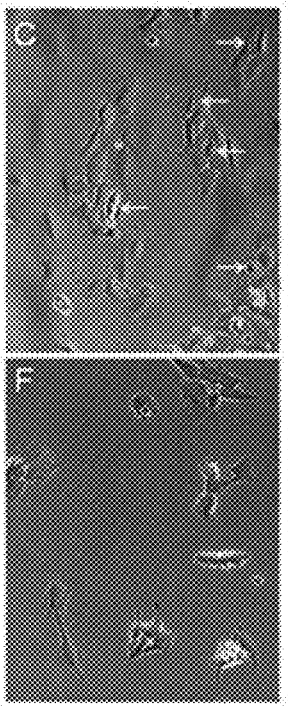
FIG. 9A   FIG. 9B   FIG. 9C
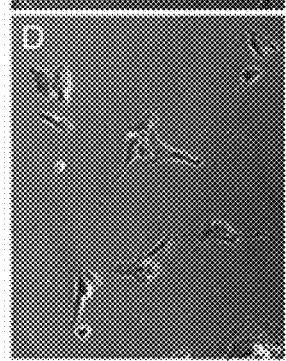 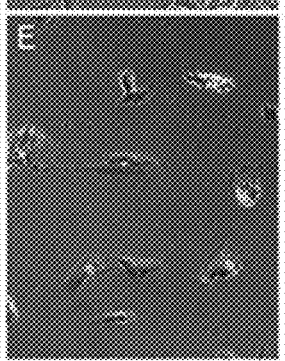 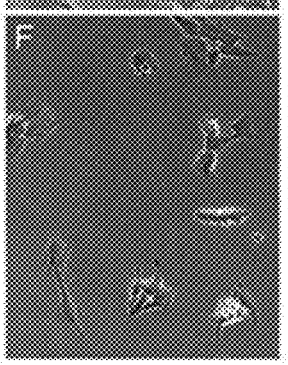
FIG. 9D   FIG. 9E   FIG. 9F FIG. 10A
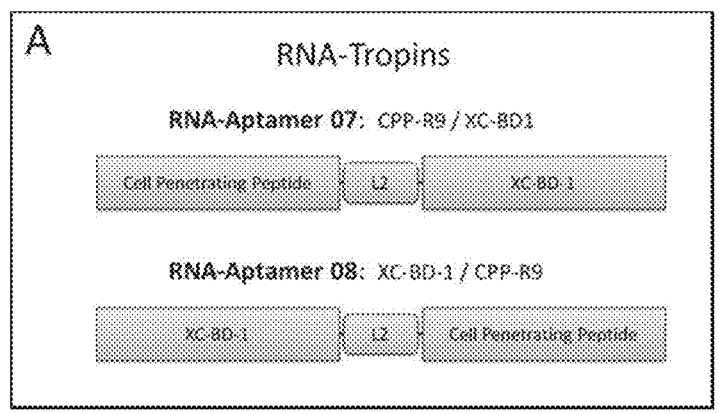
FIG. 10B          FIG. 10C
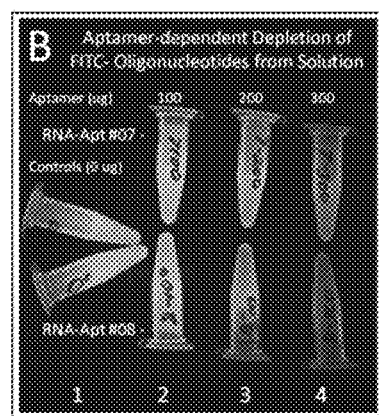 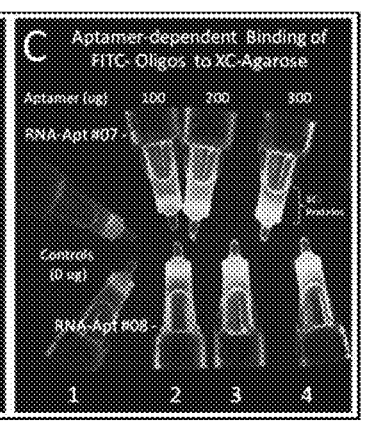

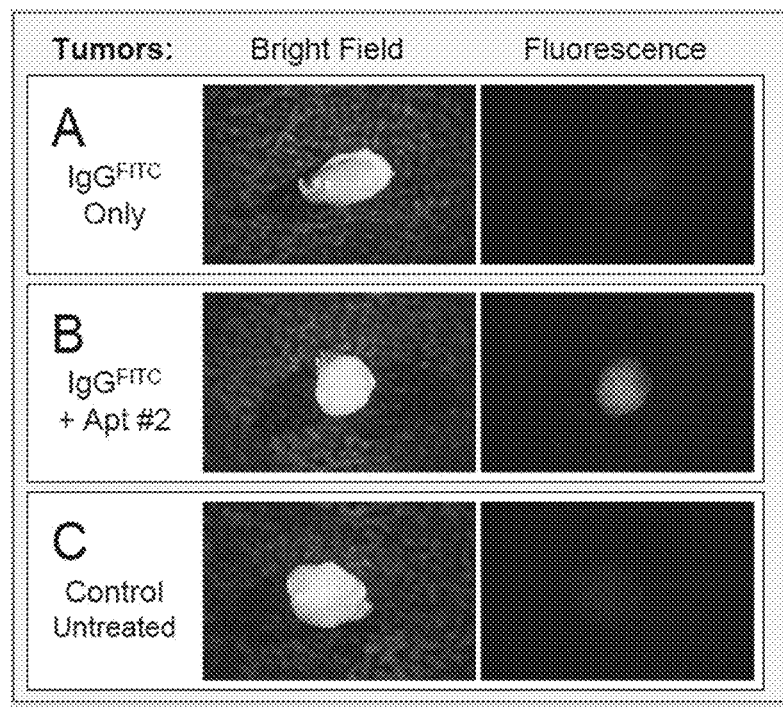
FIG. 11A
FIG. 11B
FIG. 11C
FIG. 12
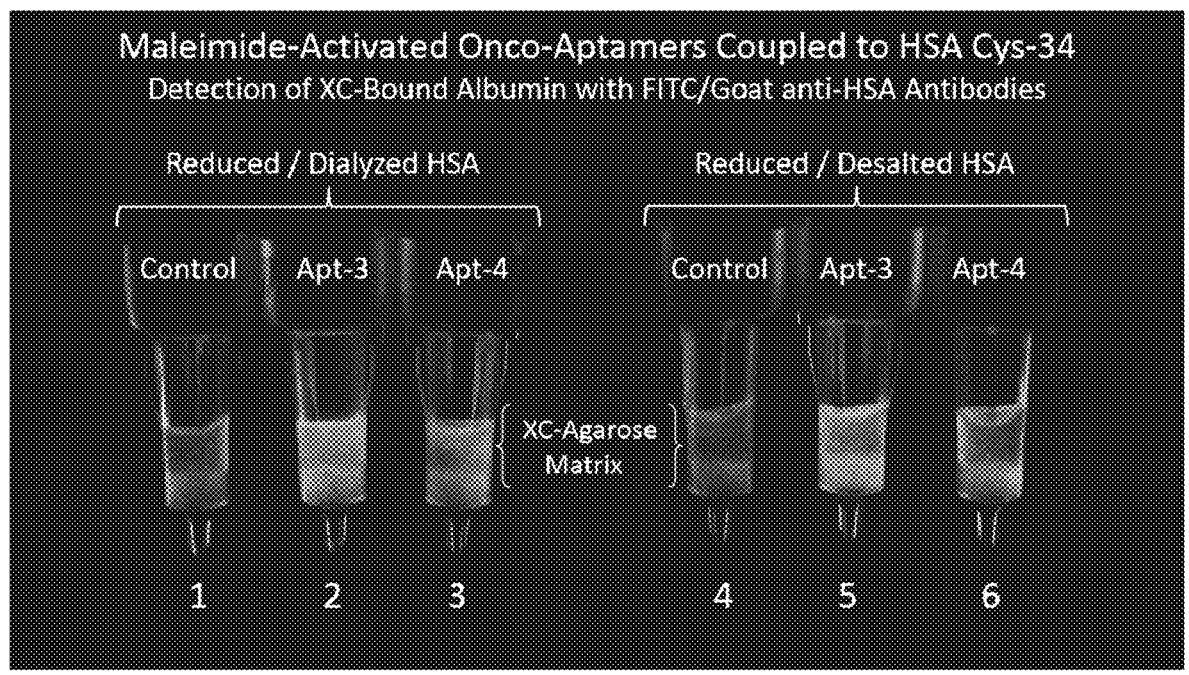

FIG. 13
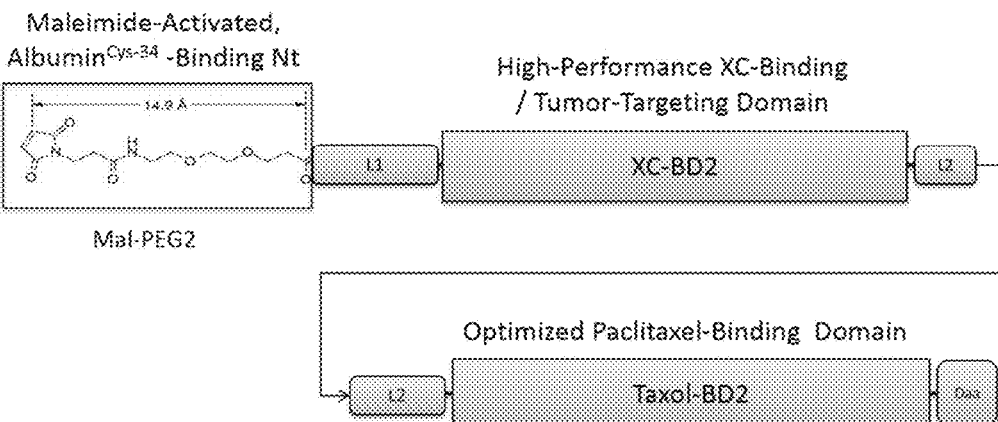
FIG. 14A
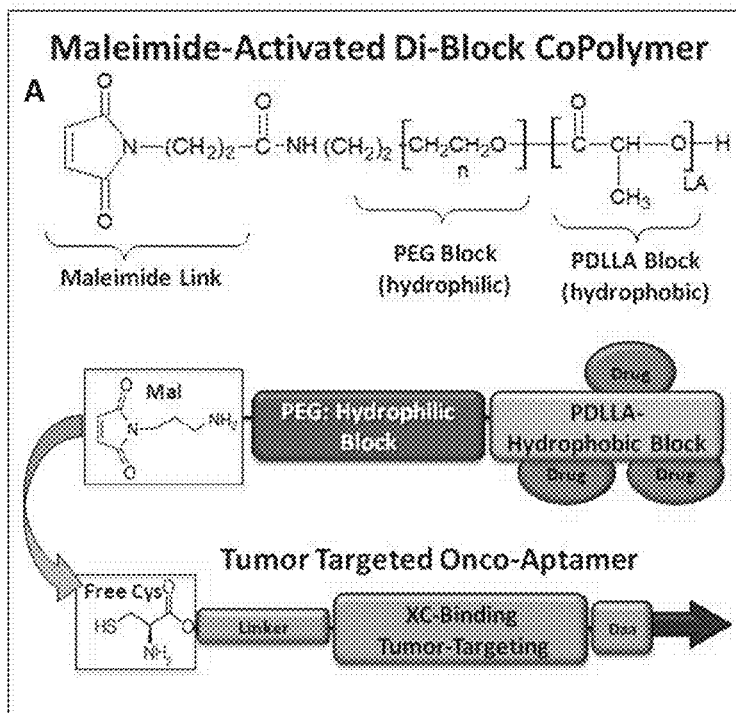
FIG. 14B
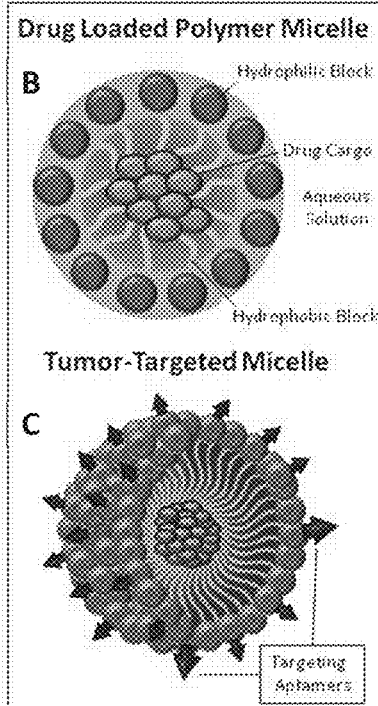
FIG. 14C

FIG. 15A
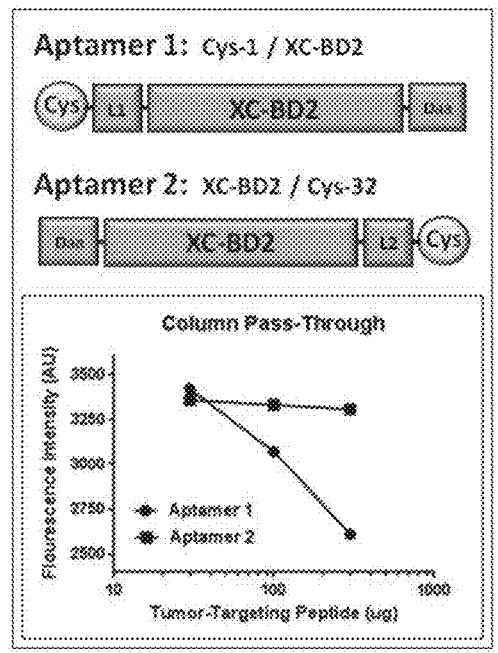
FIG. 15B
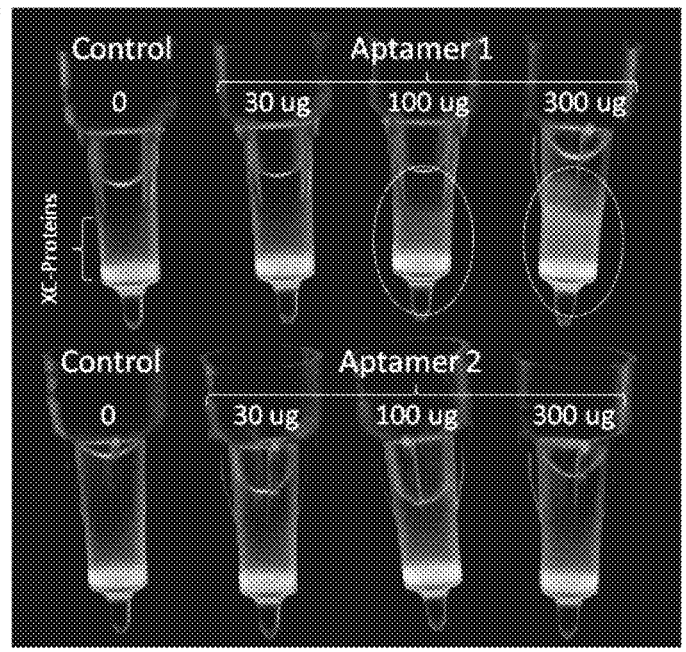
FIG. 15C
FIG. 16A
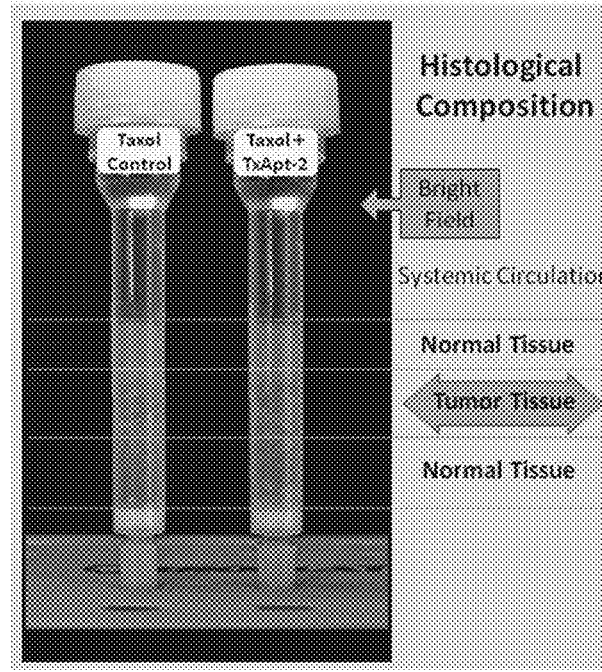
FIG. 16B
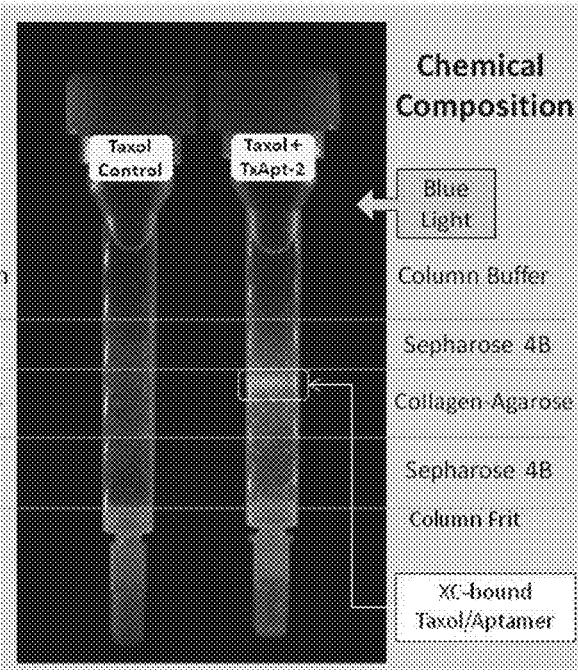

TARGETING OF PHARMACEUTICAL AGENTS TO PATHOLOGIC AREAS USING BIFUNCTIONAL FUSION POLYPEPTIDES

CROSS-REFERENCE TO RELATED APPLICATIONS

This application is a divisional of U.S. patent application Ser. No. 14/869,776, filed Sep. 29, 2015, which claims the benefit of U.S. Provisional Application Ser. No. 62/056,859, filed on Sep. 29, 2014; 62/103,489, filed on Jan. 14, 2015; and 62/214,752, filed on Sep. 4, 2015. The entire contents of the foregoing are incorporated herein by reference.

TECHNICAL FIELD

This invention relates to new compositions and methods capable of selective and efficient targeting of pharmaceutical agents to pathological areas such as cancerous lesions.

BACKGROUND

Cancer is the second most common cause of death in the US, claiming 580,000 Americans per year, more than 1,500 people each day. The number of new cancer patients diagnosed in 2012 was over 1.6 million in the U.S. alone, not including patients with noninvasive cancers and/or skin cancers. The National Institutes of Health (NIH) estimated the overall annual costs of cancer care at more than $227 billion (in 2007): including $89 billion for direct medical costs. Sales of cancer drugs in general doubled between 2005 and 2010, with conservative growth estimates of 8 to 10% per year, reaching $93 billion by 2016. Much of the overall healthcare costs of treating cancer are derived from management of the deleterious side effects of radiation and conventional chemotherapy. Nonetheless, the chemotherapy market is currently the fastest growing segment of the pharmaceutical industry, with recent estimates topping $50 billion (in 2012) and rising. Likewise, the global market for therapeutic antibodies (targeted biologics) is estimated to rise from $40 billion to $58 billion by the year 2016. However, these current cancer therapies, including surgery, systemic chemotherapy, radiation therapy, risk factor modification, are often clinically insufficient and/or unacceptably toxic. The systemic toxicities of many FDA-approved chemotherapeutic agents are a result of the non-specific distribution of these cytocidal agents in the body, which kills both cancer cells and normal cells and negatively impacts the treatment regimen and patient outcome.

SUMMARY

The present disclosure is based, at least in part, on the development of new bifunctional fusion polymers that include at least two functional domains: (i) sequences that bind to the Exposed Collagenous (XC-) proteins present in pathological areas such as cancerous lesions, and (ii) sequences that bind directly or indirectly to a particular class of chemotherapeutic or biologic agents, for example, paclitaxel, monoclonal antibodies, growth factors, or small interfering RNA (siRNA). The present disclosure is also based, at least in part, on the development of new bifunctional fusion nanoparticles that include at least two portions: (i) sequences that bind to the Exposed Collagenous (XC-) proteins present in pathological areas, and (ii) a nanoparticle that non-covalently sequesters chemotherapeutic and/or biologic agents, for example agents with hydrophobic or hydrophilic characteristics or nucleic acids. The bifunctional properties of these engineered fusion polymers and nanoparticles may enable selective and efficient targeting of the widely used chemotherapeutic and biologic agents to abnormal, diseased, or degenerative tissues such as tumors, allowing lower doses of these agents to become more effective at killing cancer cells and associated blood supply. Targeting is achieved by combining a tumor-targeting functional domain with a high-affinity, non-covalent drug-binding domain of the fusion polymer or with a nanoparticle of the fusion nanoparticle, generating drug complexes with improved biodistribution. Targeted delivery of drugs using the fusion peptide or nanoparticle disclosed herein can reduce systemic toxicity and side effects by sequestering the drugs in the tumor microenvironment and sparing normal cells and tissues from the toxicity of the drugs. Moreover, by targeting a common histopathologic property of primary tumors and metastatic lesions, the drug delivery systems described herein can (i) bind and carry one or more therapeutic drugs, in some instances upon simple mixing, and (ii) seek out and accumulate in the diseased/cancerous tissues following intravenous infusion. Thus, the fusion peptides and nanoparticles described herein may make conventional chemotherapeutic and biologic agents more efficient with great efficacy while lessening unwanted side effects, improving the overall Therapeutic Index and patient survival. These fusion polymers and nanoparticles can also include linker segments and/or flanking sequences to improve the functionality, pharmacokinetics, stability, and/or pharmacodynamics of the targeted drug delivery.

Provided herein are fusion polymers that include (i) an aptamer sequence that binds to exposed collagenous (XC) proteins present in pathological areas, including cancerous lesions, and (ii) an aptamer sequence that binds to a drug or biologic agent with therapeutic properties. In some embodiments, the collagen-binding sequence is derived from a collagen-binding domain found in von Willebrand factor, or a conservative variation thereof, which retains collagen-binding activity. For example, the collagen-binding sequence can include the minimal decapeptide Trp-Arg-Glu-Pro-Ser-Phe-Met-Ala-Leu-Ser (SEQ ID NO: 1) or Trp-Arg-Glu-Pro-Gly-Arg-Met-Glu-Leu-Asn (SEQ ID NO: 2). The drug can be a cytotoxic or cytostatic agent used for chemotherapy (e.g., a chemotherapeutic agent). In some embodiments, the drug is a monoclonal antibody or a growth factor. In some embodiments, the drug is an RNA or an siRNA. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of a pharmaceutical composition described herein. The cancer can be a primary or metastatic cancer e.g., colorectal cancer, breast cancer, brain cancer, non-small cell lung cancer, pancreatic cancer, prostate cancer, a sarcoma, a carcinoma, or a melanoma.

In some aspects, the fusion polymers described herein include (i) an aptamer sequence that binds to XC proteins present in solid tumors, and (ii) an aptamer sequence that binds to a drug, e.g., an angiogenesis modulating agent, e.g., for directly or indirectly affecting endothelial cell and/or tumor cell proliferation. The angiogenesis modulating agent can be selected from: growth factors including vascular endothelial growth factor (VEGF), epidermal growth factor (EGF), hepatocyte growth factor (HGF), platelet derived endothelial cell growth factor (PD-ECGF), platelet derived growth factor (PDGF); insulin-like growth factor (IGF), interleukin-8, growth hormone, angiopoietin, acidic and basic fibroblast growth factors (FGFs), transforming growth factor alpha (TGF-alpha.), an enzyme, an enzymatic inhibitor, and/or an antibody specific for these growth factors and their receptors.

In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the angiogenesis modulating agent is a monoclonal antibody (mAb) and the resulting onco-aptamer is referred to as a mAb-Tropin or mAb/onco-aptamer. In some embodiments, the angiogenesis modulating agent is directed against VEGF or specifically binds VEGF, for example, the angiogenesis modulating agent can be bevacizumab, aflibercept, or rilonacept. In some embodiments, the angiogenesis modulating agent can inhibit or trap VEGF when VEGF passes through a collagen-agarose column that contains collagen-bound onco-aptamer/mAb complexes. In some embodiments, the angiogenesis modulating agent inhibits vascular endothelial cell proliferation. In some embodiments, the mAb-Tropins or mAb/onco-aptamers are injected systemically to a subject and bind to exposed collagenous (XC) proteins found abundantly in tumors undergoing tumor invasion, metastasis, stroma formation and neoangiogenesis. In some embodiments, the mAb-Tropins or mAb/onco-aptamers are injected systemically to inhibit tumor growth by inhibiting tumor endothelial cell proliferation. In some embodiments, the mAb-Tropins or mAb/onco-aptamers are injected systemically for the treatment of a wide variety of primary and metastatic cancers, including but not restricted to colorectal cancer, breast cancer, brain tumors, sarcoma, carcinoma, and melanoma. In some embodiments, a pharmaceutical composition comprises, consists essentially of, or consists of, the fusion polymer and a pharmaceutically acceptable carrier.

In some embodiments, the angiogenesis modulating agent is a chemotherapeutic agent used in a metronomic regimen to induce anti-angiogenesis.

In some embodiments the aptamer that binds to a drug, or drug binding domain, is a chemotherapeutic agent binding domain and the drug is a chemotherapeutic agent. For example, the chemotherapeutic agent can be, but is not restricted to, paclitaxel, docetaxel, or nab-paclitaxel, and the resulting onco-aptamer is referred to as Taxol-Tropin or Adaptane-Tx. In some embodiments, a pharmaceutical composition comprises, consists essentially of, or consists of, the fusion polymer, the chemotherapeutic agent and a pharmaceutically acceptable carrier. In some embodiments, Taxol-Tropin or Adaptane-Tx is injected systemically to a subject to inhibit tumor growth by inhibiting tumor endothelial cell proliferation. In some embodiments, Taxol-Tropin or Adaptane-Tx is injected systemically to a subject for the treatment of a wide variety of primary and metastatic cancers, including but not restricted to colorectal cancer, breast cancer, brain tumors, non-small cell lung cancer, pancreatic cancer and prostate cancer.

In some embodiments, the drug binding domain of the fusion polymer is a chemotherapeutic agent binding domain, the drug is a chemotherapeutic agent and the chemotherapeutic agent is a monoclonal antibody (mAb). In some embodiments, the chemotherapeutic agent comprises, consists essentially of, or consists of a mAb that is selected from the group consisting of an anti-CTLA-4, anti-PD-1, and anti-PD-L1 antibody. In some embodiments, the mAb is Ipililumab, Nivolumab, Pembrolizumab, or any combination thereof. In some embodiments, a pharmaceutical composition comprises, consists essentially of, or consists of, the fusion polymer, a mAb and a pharmaceutically acceptable carrier. Also provided are methods of treating cancer in a subject, the method comprising, consisting essentially of, or consisting of: administering to a subject in need of such treatment the fusion polymer comprising (a) a collagen-binding domain comprising an amino acid sequence, and (b) a mAb-binding domain in an amount sufficient to treat the tumor; and a mAb bound by the mAb-binding domain, wherein the mAb bound to the fusion polymer activates the immune response within the tumor. The cancer can be a primary or metastatic cancer as described herein.

In some embodiments, the drug or biologic agent is a siRNAs and the resulting fusion polymer is referred to as RNA-Tropin. In some embodiments, the siRNA-binding domain comprises, consists essentially of, or consists of the amino acid sequence of SEQ ID NO: 29 or SEQ ID NO: 30. In some embodiments, the RNA-Tropin fusion polymer comprises, consists essentially of, or consists of the amino acid sequence of SEQ ID NO: 35, SEQ ID NO: 36, SEQ ID NO:37, SEQ ID NO: 38, or SEQ ID NO: 55. In some embodiments, a pharmaceutical composition comprises, consists essentially of, or consists of, the fusion polymer, the RNA and a pharmaceutically acceptable carrier. In some embodiments, a subject can be treated with the RNA-Tropin, wherein it is injected systemically for the treatment of a wide variety of primary and metastatic cancers, including but not restricted to colorectal cancer, breast cancer, brain tumors, non-small cell lung cancer, pancreatic cancer, prostate cancer, sarcoma, carcinoma, and melanoma.

In some embodiments, the bifunctional fusion polymer binds to collagen and paclitaxel. The fusion polymer can comprise, consist essentially of, or consist of, (a) a collagen-binding domain comprising an amino acid sequence of SEQ ID NO: 1 or SEQ ID NO: 2; and (b) a paclitaxel-binding domain comprising an amino acid sequence selected from the group consisting of: Arg-Gly-Val-Gly-Ile-Met-Lys-Ala-Cys-Gly-Arg-Thr-Arg-Val-Thr-Ser (SEQ ID NO: 3); Arg-Gly-Val-Gly-Ile-Met-Lys-Ala-Cys-Gly-Arg-Thr-Arg-His-Thr-Val-Arg (SEQ ID NO: 4); Arg-Gly-Val-Gly-Ile-Met-Lys-Ala-Cys-Gly-Arg-Thr-Arg-His-Thr-Val-Arg-(D-Met)-Gly (SEQ ID NO: 5); and Ala-Phe-Met-Thr-Lys-Thr-Met-Glu-Cys-Gly-Arg-Thr-Arg-His-Thr-Val-Arg-Met-Gly (SEQ ID NO: 6). In some embodiments, the fusion polymer further includes one or more linkers/spacers. For example, the fusion polymer can have one or more linkers comprising an amino acid sequence such as Gly-Gly-Ser-Gly (SEQ ID NO: 7), Arg-Arg-Gly-Val-His-Val-Gly (SEQ ID NO: 8), (D-Arg)-(D-Arg)-Gly-Val-His-Val-Gly (SEQ ID NO: 9), or Lys-Gly-Arg-Arg-Gly-Val-His-Val-Gly (SEQ ID NO: 10), or variants of these sequences. In some embodiments, the fusion polymer is acetylated, amidated, and/or PEGylated at N- or C-terminus. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the collagen-binding and paclitaxel-binding fusion polymer comprises, consists essentially of, or consists of, an amino acid sequence selected from the group consisting of: Arg-Arg-Gly-Val-His-Val-Gly-Trp-Arg-Glu-Pro-Ser-Phe-Met-Ala-Leu-Ser-Met-Pro-His-Gly-Gly-Ser-Gly-Arg-Gly-Val-Gly-Ile-Met-Lys-Ala-Cys-Gly-Arg-Thr-Arg-Val-Thr-Ser-Ala-Gly-Ser-Gly (SEQ ID NO: 11); (D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Arg-Gly-Val-Gly-Ile-Met-Lys-Ala-Cys-Gly-Arg-Thr-Arg-His-Thr-Val-Arg-(D-Met)-Gly (SEQ ID NO: 12); Lys-Gly-Arg-Arg-Gly-Val-His-Val-Gly-Trp-Arg-Glu-Pro-Gly-Arg-Met-Glu-Leu-Asn-Met-Pro-His-Gly-Gly-Ser-Gly-Arg-Gly-Val-Gly-Ile-Met-Arg-Ala-Cys-Gly-Arg-Thr-Arg-His-Thr-Val-Arg-(D-Met)-Gly (SEQ ID NO: 13), and (D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Arg-Gly-Val-Gly-Ile-Met-Lys-Ala-Cys-Gly-Arg-Thr-Arg-His-Thr-Val-Arg-Met-Gly-(D-Pro)-(D-Thr) (SEQ ID NO: 14).

In some embodiments, the bifunctional fusion polymer binds to collagen and a therapeutic immunoglobulin such as a mAb. The fusion polymer can comprise, consist essentially of, or consist of, (a) a collagen-binding domain comprising an amino acid sequence of SEQ ID NO: 1, or SEQ ID NO: 2; and (b) an immunoglobulin-binding domain comprising the amino acid sequence of His-Trp-Arg-Gly-Trp-Val (SEQ ID NO: 15). In some embodiments, the fusion polymer further includes one or more linkers/spacers. For example, the fusion polymer can have one or more linkers comprising, consisting essentially of, or consisting of an amino acid sequence such as Gly-Gly-Gly-Gly-Gly (SEQ ID NO: 16), Gly-Gly-Ser-Gly-Gly (SEQ ID NO: 17), SEQ ID NO: 8, SEQ ID NO: 9, Cys-Gly-Arg-Arg-Gly-Val-His-Val-Gly (SEQ ID NO: 57), and Cys-Ala-Arg-Arg-Gly-Val-His-Val-Gly (SEQ ID NO: 58), or variants of these sequences. In some embodiments, the fusion polymer is acetylated, amidated, and/or PEGylated at N- or C-terminus. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the collagen-binding and immunoglobulin-binding fusion polymer comprises, consists essentially of, or consists of, an amino acid sequence selected from the group consisting of: Arg-Arg-Gly-Val-His-Val-Gly-Trp-Arg-Glu-Pro-Ser-Phe-Met-Ala-Leu-Ser-Met-Pro-His-Gly-Gly-Gly-Gly-Gly-His-Trp-Arg-Gly-Trp-Val-Gly-Gly-Gly-Gly-Gly-His-Trp-Arg-Gly-Trp-Val (SEQ ID NO: 18); (D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Gly-His-Trp-Arg-Gly-Trp-Val-Ala-Gly-Gly-Ser-Gly-Gly-His-Trp-Arg-Gly-Trp-Val-(D-Ala)-(D-Ala) (SEQ ID NO: 19); Cys-Gly-Arg-Arg-Gly-Val-His-Val-Gly-Trp-Arg-Glu-Pro-Gly-Arg-Met-Glu-Leu-Asn-Met-Pro-His-Gly-Gly-Ser-Gly-Gly-His-Trp-Arg-Gly-Trp-Val-Ala-Gly-Gly-Ser-Gly-Gly-His-Trp-Arg-Gly-Trp-Val-(D-Ala)-(D-Ala) (SEQ ID NO: 20); and Cys-Ala-Arg-Arg-Gly-Val-His-Val-Gly-Trp-Arg-Glu-Pro-Gly-Arg-Met-Glu-Leu-Asn-Met-Pro-His-Gly-Gly-Ser-Gly-Gly-His-Trp-Arg-Gly-Trp-Val-Ala-Gly-Gly-Ser-Gly-Gly-His-Trp-Arg-Gly-Trp-Val-Ala-(D-Pro)-(D-Thr) (SEQ ID NO: 21).

In some embodiments, the bifunctional fusion polymer binds to collagen and a therapeutic ribonucleic acid such as a siRNA. This fusion polymer comprises, consists essentially of, or consists of, (a) a collagen-binding domain comprising an amino acid sequence of SEQ ID NO: 1 or SEQ ID NO: 2; and (b) an RNA-binding domain comprising an amino acid sequence of Arg-Arg-Arg-Arg-Arg-Arg-Arg-Arg-Arg (SEQ ID NO: 29), or (D-Arg)-(D-Arg)-(D-Arg)-(D-Arg)-(D-Arg)-(D-Arg)-(D-Arg)-(D-Arg)-(D-Arg) (SEQ ID NO: 30). In some embodiments, the fusion polymer further includes one or more linkers/spacers. For example, the fusion polymer can have one or more linkers comprising an amino acid sequence such as Gly-Gly-Ser-Gly-Gly-Ser-Gly-Gly (SEQ ID NO: 31), Gly-Gly-Arg-Arg-Gly-Val-His-Val-Gly (SEQ ID NO: 32), SEQ ID NO: 8, SEQ ID NO: 58, Cys-Gly-Ser-Gly-Gly (SEQ ID NO: 33), and Gly-Gly (SEQ ID NO: 34), or variants of these sequences. In some embodiments, the fusion polymer is amidated, acetylated and/or PEGylated at N- or C-terminus. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the collagen-binding and RNA-binding fusion polymer comprises, consists essentially of, or consists of, an amino acid sequence selected from the group consisting of: Arg-Arg-Gly-Val-His-Val-Gly-Trp-Arg-Glu-Pro-Ser-Phe-Met-Ala-Leu-Ser-Met-Pro-His-Gly-Gly-Arg-Arg-Arg-Arg-Arg-Arg-Arg-Arg (SEQ ID NO: 35); Cys-Ala-Arg-Arg-Gly-Val-His-Val-Gly-Trp-Arg-Glu-Pro-Gly-Arg-Met-Glu-Leu-Asn-Met-Pro-His-Gly-Gly-Ser-Gly-Gly-Ser-Gly-Gly-(D-Arg)-(D-Arg)-(D-Arg)-(D-Arg)-(D-Arg)-(D-Arg)-(D-Arg)-(D-Arg)-(D-Arg) (SEQ ID NO: 36); (D-Arg)-(D-Arg)-(D-Arg)-(D-Arg)-(D-Arg)-(D-Arg)-(D-Arg)-(D-Arg)-(D-Arg)-Gly-Gly-Arg-Arg-Gly-Val-His-Val-Gly-Trp-Arg-Glu-Pro-Gly-Arg-Met-Glu-Leu-Asn-Met-Pro-His-Gly-(D-Gln)-(D-Pro)-(D-Thr) (SEQ ID NO: 37); Cys-Gly-Ser-Gly-Gly-(D-Arg)-(D-Arg)-(D-Arg)-(D-Arg)-(D-Arg)-(D-Arg)-(D-Arg)-(D-Arg)-(D-Arg)-Gly-Gly-Arg-Arg-Gly-Val-His-Val-Gly-Trp-Arg-Glu-Pro-Gly-Arg-Met-Glu-Leu-Asn-Met-Pro-His-Gly-(D-Gln)-(D-Pro)-(D- Thr) (SEQ ID NO: 38); and Arg-Arg-Arg-Arg-Arg-Arg-Arg-Arg-Arg-Arg-Arg-Gly-Val-His-Val-Gly-Trp-Arg-Glu-Pro-Ser-Phe-Met-Ala-Leu-Ser-Met-Pro-His-Gly-Gly (SEQ ID NO: 55).

In some embodiments, the bifunctional fusion polymer binds to collagen and human serum albumin (HSA), wherein the HSA can in turn bind a therapeutic agent. The fusion polymer comprises, consists essentially of, or consists of, (a) a collagen-binding domain comprising an amino acid sequence of SEQ ID NO: 1 or SEQ ID NO: 2; and (b) a human serum albumin (HSA)-binding domain that comprises a thiol-reactive maleimide group, or a peptide comprising the amino acid sequence of Thr-Arg-Ser-Phe-Cys-Thr-Asp-Trp-Pro-Ala-His-Lys-Ser-Cys-Lys-Pro-Leu (SEQ ID NO: 39), or Arg-Gln-Met-Glu-Asp-Ile-Cys-Leu-Pro-Arg-Trp-Gly-Cys-Leu-Trp-Gly-Asp (SEQ ID NO: 40). In some embodiments, the fusion polymer further includes one or more linkers/spacers as described herein, or variants of these sequences. In some embodiments, the fusion polymer is acetylated, amidated, and/or PEGylated at N- or C-terminus. In some embodiments, the fusion polymer comprises, consists essentially of, or consists of, (a) a collagen-binding tumor-targeting domain comprising an amino acid sequence of SEQ ID NO: 1 or SEQ ID NO: 2; and (b) a HSA-binding domain, wherein the HSA-binding domain comprises a thiol-reactive maleimide group covalently linked to the collagen-binding domain or a targeting peptide comprising the albumin-binding amino acid sequence of SEQ ID NO: 39 or SEQ ID NO: 40. In some embodiments, the therapeutic agent that binds to the HSA is a platinum drug. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the collagen-binding and HSA-binding fusion polymer comprises, consists essentially of, or consists of, an amino acid sequence selected from the group consisting of: (D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Gly-Ser-Gly-Gly-Thr-Arg-Ser-Phe-Cys-Thr-Asp-Trp-Pro-Ala-His-Lys-Ser-Cys-Lys-Pro-Leu-(D-Arg)-(D-Ala) (SEQ ID NO: 41); (D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Gly-Ser-Gly-Gly-Arg-Gln-Met-Glu-Asp-Ile-Cys-Leu-Pro-Arg-Trp-Gly-Cys-Leu-Trp-Gly-Asp-(D-Glu)-(D-Asp) (SEQ ID NO: 42); Maleimide-PEG2-Ser-Gly-Gly-Ser-Gly-Ala-Arg-Arg-Gly-Val-His-Val-Gly-Trp-Arg-Glu-Pro-Gly-Arg-Met-Glu-Leu-Asn-Met-Pro-His-Gly-(D-Gln)-(D-Pro)-(D-Thr) (SEQ ID NO: 43), and (D-Ala)-(D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Gly-Ser-Lys-PEG2-Maleimide (SEQ ID NO: 44).

In some embodiments, the collagen-binding and drug-binding fusion polymer further comprises a HSA-binding domain, e.g., as a third portion. The HSA-binding domain comprises, consists essentially of, or consists of, an amino acid sequence selected from the group consisting of SEQ ID NO: 39 or SEQ ID NO: 40. In some embodiments, the fusion polymer further includes one or more linker/spacers. For example, the fusion polymer can have one or more linkers wherein the one or more linkers connect the HSA-binding, XC-binding, and the drug-binding domains or are connected to the terminus of the polymer. In some embodiments, the fusion polymer is acetylated, amidated and/or PEGylated at N- or C-terminus. In some embodiments, the drug-binding domain is a chemotherapeutic agent binding domain and the drug is a chemotherapeutic agent. In some embodiments, the chemotherapeutic agent is paclitaxel, docetaxel, or nab-paclitaxel. In some embodiments, a pharmaceutical composition comprises, consists essentially of, or consists of, the fusion polymer and a pharmaceutically acceptable carrier. Also included are methods of treating cancer in a subject. The methods include, e.g., administering to the subject a pharmaceutically effective amount of the pharmaceutical composition described herein. The cancer can be a primary or metastatic cancer as described herein.

In some embodiments, the fusion polymer further comprises a PEG moiety or a thio-reactive maleimide group, wherein the PEG moiety or the thio-reactive group is linked to the N- or C-terminus of the polymer. For example, the fusion polymer can comprise, consist essentially of, or consist of, an amino acid sequence of miniPEG-Ser-Gly-Gly-Ser-Gly-Ala-Arg-Arg-Gly-Val-His-Val-Gly-Trp-Arg-Glu-Pro-Gly-Arg-Met-Glu-Leu-Asn-Met-Pro-His-Gly-Gly-Ser-Arg-Gly-Val-Gly-Ile-Met-Lys-Ala-Cys-Gly-Arg-Thr-Arg-His- Thr-Val-Arg-(D-Met)-Gly-(D-Ser) (SEQ ID NO: 27), wherein (D-Aaa) designates D-amino acids. The fusion polymer can further comprise one or more linkers, where the one or more linkers join the different functional domains (e.g., the HSA-binding domain, the XC-binding domain, or the drug-binding domain) or are connected to the terminus of the polymer. The one or more linkers comprises, consists essentially of, or consists of, an amino acid sequence selected from the group consisting of Gly-Gly-Gly-Gly (SEQ ID NO: 22), SEQ ID NO: 7, Ser-Gly-Gly-Ser-Gly (SEQ ID NO: 23), SEQ ID NO: 17, Ser-Gly-Gly-Ser-Gly-Ser (SEQ ID NO: 24), Gly-Gly-Ser-Gly-Gly-Ser-Lys (SEQ ID NO: 25), SEQ ID NO: 31, and Gly-Ser-Gly-Gly-Ser-Gly-Gly-Ser-Gly (SEQ ID NO: 26), wherein the one or more linkers connect the XC-binding and drug-binding domains or are connected to the terminus of the polymer. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some aspects, the fusion polymer comprises a tumor-targeting sequence that binds to exposed collagen (XC) proteins, and a di-block copolymer that comprises a distinct hydrophilic block and a distinct hydrophobic block. The fusion polymer can further comprise one or more linkers. The one or more linkers can comprise, consist essentially of, or consist of, an amino acid sequence selected from the group consisting of SEQ ID NO: 22, SEQ ID NO: 7, SEQ ID NO: 23, SEQ ID NO: 17, SEQ ID NO: 24, SEQ ID NO: 25, SEQ ID NO: 31, SEQ ID NO: 26 and SEQ ID NO: 9, wherein a first linker is bound to the N-terminus of the tumor-targeting aptamer and further comprises a cysteine residue on the N-terminus of the first linker, and a second linker connects the hydrophilic terminus of the di-block to a maleimide-group, wherein the cysteine residue of the first linker and the maleimide-group of the second linker are covalently linked, thereby connecting the tumor-targeting aptamer and the di-block copolymer, making the fusion polymer. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments the hydrophilic block comprises, consists essentially of, or consists of, a hydrophilic polymer. Exemplary hydrophilic polymers include poly-ethylene glycol (PEG), poly-N-vinyl pyrrolidone (PVP), and poly-N-isopropyl acrylamide (pNIPAM or NIPAM), or other variants (see Sutton et al., Pharmaceutical Res., 2007, 24:1029-1045 incorporated herein in its entirety).

In some embodiments the hydrophobic block comprises, consists essentially of, or consists of, a hydrophobic polymer. Exemplary hydrophobic polymers include alkyl chain, poly-L-lactide (PLLA), poly-D,L-lactide (PDLLA), poly-caprolactone (PCL), poly-D,L-lactic-co-glycolic acid (PLGA), poly-delta-verolactone (PVL), and poly-L-histadine (pHis) (see Shuai et al., 2004, J Controlled Release, 98:415-426; Sutton et al., Pharmaceutical Res., 2007, 24:1029-1045 which are both incorporated herein in their entirety).

In some embodiments the fusion polymer comprises, consists essentially of, or consists of, the di-block copolymer that comprises Maleimide-[PEG]$_n$-[PDLLA]$_m$, wherein n is at least 1 and m is at least 1. In some embodiments the tumor targeting aptamer sequence comprises, consists essentially of, or consists of the amino acid sequenced selected from the group consisting of Cys-Gly-Ser-Gly-Gly-Ser-Gly-Gly-Ser- Gly-Ala-Arg-Arg-Gly-Val-His-Val-Gly-Trp-Arg-Glu-Pro-Gly-Arg-Met-Glu-Leu-Asn-Met-Pro-His-Gly-(D-Gln)-(D-Pro)-(D-Thr)-amide (SEQ ID NO: 56) or acetyl-(D-Ala)-(D-Arg)-(D-Arg)-Gly-Val-His-Val-Gly-Trp-Arg-Glu-Pro-Gly-Arg-Met-Glu-Leu-Asn-Met-Pro-His-Gly-Gly-Ser-Gly-Gly-Ser-Gly-Gly-Ser-Gly-Cys (SEQ ID NO: 28), wherein (D-Aaa) designate D-amino acids.

Also provided herein are nanoparticles or bifunctional fusion nanoparticles, e.g., micelles and/or liposomes that include the fusion polymers described herein. In some aspects, a nanoparticle of the present invention comprises, consists essentially of, or consists of, a micelle having a hydrophobic interior and a hydrophilic surface, and that includes at least one fusion polymer that comprises a collagen-binding domain and a di-block copolymer and wherein the tumor targeting domain of the at least one fusion polymer extends outwardly from the hydrophilic surface of the micelle. This arrangement allows the tumor targeting domain extending from the micelle surface to bind to XC proteins while associated with the micelle. In some embodiments, the micelle comprises, consists essentially of, or consists of, a plurality of the fusion polymers and wherein the fusion polymers comprise at least or about $1/10^{th}$ (at least or about $2/10^{th}$, $3/10^{th}$, $4/10^{th}$, $5/10^{th}$, $6/10^{th}$, $7/10^{th}$, $8/10^{th}$ or at least or about $9/10^{th}$, e.g., $10/10^{th}$) of the total number of polymers that comprise the micelle. In some embodiments, the tumor targeting domain comprises, consists essentially of, or consists of, an amino acid sequence of SEQ ID NO: 1 or SEQ ID NO: 2 and in some embodiments, the tumor targeting domain binds to exposed collagenous proteins that are present in solid tumors. In some embodiments, a pharmaceutical composition comprises, consists essentially of, or consists of, the fusion nanoparticle and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some aspects, a drug-delivery or bifunctional fusion nanoparticle comprises, consists essentially of, or consists of, a micelle comprising at least or about one fusion polymer and a drug sequestered inside the hydrophobic interior of the micelle. In some embodiments, a pharmaceutical composition comprises, consists essentially of, or consists of, the fusion nanoparticle and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the drug sequestered inside the micelle comprises, consists essentially of, or consists of, a drug such as a hydrophobic drug, a hydrophilic drug, a nucleic acid, a Taxane, doxorubicin, epirubicin, a platinum drug, R547, a cyclin-dependent kinase inhibitor, TGX-221, a PI-3 kinase inhibitor, captothecin, gemcitabine, 5-fluouracil, rifampicin, tamoxifen, ellipticin, ethotrexate, daunomycin, estrogen, curcumin, and an siRNA, or any mixture thereof. In some embodiments the drug is a hydrophobic drug that is sequestered in the hydrophobic interior of the micelle.

Also provided are methods of making a fusion polymer that comprises a tumor targeting aptamer sequence that binds to exposed collagenous (XC) proteins, and a di-block copolymer comprising a hydrophilic block and a hydrophobic block, comprising: (a) providing the tumor targeting aptamer sequence and a first linker that is bound to the N-terminus of the tumor-targeting aptamer and further comprises a cysteine residue on the N-terminus of the first linker; (b) providing the di-block copolymer and a second linker that is disposed between and linked to both the terminus hydrophilic block of the di-block and a maleimide-group; and (c) combining (a) and (b) under conditions such that the maleimide-group of (b) reacts with the thiol group of the cysteine residue of (a) to form a covalent bond between (a) and (b), thereby creating the fusion polymer.

Also provided are methods of making a micelle that comprises, consists essentially of, or consists of a hydrophobic interior and a hydrophilic surface and at least one fusion polymer comprising (i) a tumor targeting domain that binds to exposed collagenous (XC) proteins, and (ii) a di-block copolymer comprising a hydrophilic block and a hydrophobic block, wherein the tumor targeting domain of the at least one fusion polymer extends outwardly from the hydrophilic surface of the micelle, such that the tumor targeting domain can bind to XC proteins while associated with the micelle. The method of making a micelle can comprise: (a) providing a first and a second plurality of di-block copolymers, each comprising a hydrophobic block and a hydrophilic block, wherein the di-block copolymers of the second plurality each comprise a linker bound to the terminus of the hydrophilic block, and wherein a maleimide group is bound to the linker terminus that is unbound to the hydrophilic block; (b) mixing the first and second plurality of di-block copolymers to thereby form a micelle; (c) providing a tumor-targeting domain that binds to exposed collagenous proteins and that comprises a cysteine residue on a terminus of the domain; and (d) combining the micelle of (b) with the tumor-targeting domain of (c) under conditions such that an activated maleimide of the di-block copolymers of the second plurality in the micelle reacts with the cysteine residue of the tumor-targeting domain, thereby connecting the tumor-targeting domain and the micelle.

In some embodiments, the method of making a micelle comprises: (a) providing a first and a second plurality of di-block copolymers, each comprising a hydrophobic block and a hydrophilic block, wherein the di-block copolymers of the second plurality each comprise a linker bound to the terminus of the hydrophilic block, and wherein a maleimide group is bound to the linker terminus that is unbound to the hydrophilic block; (b) providing a tumor-targeting domain that binds to exposed collagenous proteins and that comprises a cysteine residue on a terminus of the domain; (c) combining the second plurality of di-block copolymers of (a) with the tumor-targeting domain of (b) under conditions such that the activated maleimide of the di-block copolymers reacts with the cysteine residue of the tumor-targeting domain, thereby connecting the tumor-targeting domain and the di-block copolymer and creating a fusion polymer; and (d) mixing the fusion polymer of (c) with the first plurality of di-block copolymers to thereby form a micelle.

In some embodiments, the method of making a micelle further comprises, during mixing, adding a therapeutic agent, e.g., an agent described herein, such as an anticancer agent, under conditions sufficient to form a micelle that encapsulates the therapeutic agent, to thereby make a drug-delivery nanoparticle. In some embodiments, the therapeutic agent is a hydrophobic drug that is sequestered in the hydrophobic interior of the micelle.

Also provided are methods of making a drug-delivery nanoparticle that comprises, consists essentially of, or consists of (1) a micelle comprising a hydrophobic interior and a hydrophilic surface and at least one fusion polymer comprising (i) a tumor targeting domain that binds to exposed collagenous (XC) proteins, and (ii) a di-block copolymer comprising a hydrophilic block and a hydrophobic block, wherein the tumor targeting domain of the at least one fusion polymer extends outwardly from the hydrophilic surface of the micelle, such that the tumor targeting domain can bind to XC proteins while associated with the micelle; and (2) a drug sequestered in the hydrophobic interior of the micelle, comprising (a) providing the drug; (b) providing the micelle; and (c) mixing the drug and the micelle to allow association of the micelle with the drug, thereby forming a drug-delivery nanoparticle.

Also provided is a fusion polymer that comprises, consists essentially of, or consists of, a tumor targeting aptamer sequence that binds to exposed collagenous (XC) protein, and a multi-block polymer comprising sequentially a first hydrophilic block, a first hydrophobic block, a second hydrophobic block, and a second hydrophilic block. The fusion polymer can further comprise one or more linkers as described herein, wherein the one or more linkers link the tumor targeting aptamer and the multi-block polymer or are attached to the terminus of the polymer. In some embodiments, the linkers comprise, consist essentially of, or consist of an amino acid sequence selected from the group consisting of SEQ ID NO: 22, SEQ ID NO: 7, SEQ ID NO: 23, SEQ ID NO: 17, SEQ ID NO: 24, SEQ ID NO: 25, SEQ ID NO: 31, SEQ ID NO: 26 and SEQ ID NO: 9. In some embodiments, the multi-block polymer comprises Maleimide-$[PEG]_n$-$[PDLLA]_m$-$[PDLLA]_m$-$[PEG]_n$, wherein n is at least 1 and m is at least 1. In some embodiments, a pharmaceutical composition comprises, consists essentially of, or consists of, the fusion polymer and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments the hydrophilic block comprises, consists essentially of, or consists of, a hydrophilic polymer. Exemplary hydrophilic polymers include poly-ethylene glycol (PEG), poly-N-vinyl pyrrolidone (PVP), and poly-N-isopropyl acrylamide (pNIPAM or NIPAM), or other variants (see Sutton et al., Pharmaceutical Res., 2007, 24:1029-1045 incorporated herein in its entirety).

In some embodiments the hydrophobic block comprises, consists essentially of, or consists of, a hydrophobic polymer. Exemplary hydrophobic polymers include alkyl chain, poly-L-lactide (PLLA), poly-D,L-lactide (PDLLA), poly-caprolactone (PCL), poly-D,L-lactic-co-glycolic acid (PLGA), poly-delta-verolactone (PVL), and poly-L-histadine (pHis) (see Shuai et al., 2004, J Controlled Release, 98:415-426; Sutton et al., Pharmaceutical Res., 2007, 24:1029-1045 which are both incorporated herein in their entirety).

In some embodiments a bifunctional fusion nanoparticle comprises, consists essentially of, or consists of, a liposome comprising a lipid bilayer having a hydrophilic exterior surface and an aqueous interior and comprising at least one fusion polymer comprising (i) a tumor targeting domain that binds to exposed collagenous (XC) proteins, and (ii) a multi-block polymer comprising sequentially a first hydrophilic block, a first hydrophobic block, a second hydrophobic block, and a second hydrophilic block, wherein the tumor targeting domain of the at least one fusion polymer extends outwardly from the hydrophilic exterior surface of the liposome, such that the tumor targeting domain can bind to XC proteins while associated with the liposome. In some embodiments, the liposome comprises, consists essentially of, or consists of, a plurality of the fusion polymers and wherein the fusion polymers comprise at least or about $\frac{1}{10}^{th}$ (at least or about $\frac{2}{10}^{ths}$, $\frac{3}{10}^{ths}$, $\frac{4}{10}^{ths}$, $\frac{5}{10}^{ths}$, $\frac{6}{10}^{ths}$, $\frac{7}{10}^{ths}$, $\frac{8}{10}^{ths}$ or at least or about $\frac{9}{10}^{th}$, e.g., $\frac{10}{10}^{ths}$, i.e., all) of the total number of polymers that comprise the liposome. In some embodiments, the tumor targeting aptamer comprises, consists essentially of, or consists of, SEQ ID NO: 1 or SEQ ID NO: 2 and in some embodiments, the tumor targeting domain binds to XC proteins present in solid tumors. In some embodiments, a pharmaceutical composition comprises, consists essentially of, or consists of, the fusion nanoparticle and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the drug-delivery or bifunctional fusion nanoparticle comprises, consists essentially of, or consists of, a liposome comprising at least or about one fusion polymer and at least one drug sequestered inside the aqueous interior of the shell lipid bilayer of the liposome. In some embodiments the drug-delivery or bifunctional fusion nanoparticle comprises, consists essentially of, or consists of, a liposome comprising at least or about one fusion polymer and at least one drug sequestered inside the lipid bilayer of the liposome. In some embodiments, a pharmaceutical composition comprises, consists essentially of, or consists of, the fusion nanoparticle and a pharmaceutically acceptable carrier. Also included are methods of treating cancer in a subject that include, e.g., administering to the subject a pharmaceutically effective amount of the pharmaceutical composition described herein. The cancer can be a primary or metastatic cancer as described herein.

In some embodiments, the drug sequestered inside the liposome comprises, consists essentially of, or consists of, a drug selected from the group consisting of: a hydrophobic drug, a hydrophilic drug, a nucleic acid, a Taxane, doxorubicin, epirubicin, a platinum drug, R547, a cyclin-dependent kinase inhibitor, TGX-221, a PI-3 kinase inhibitor, captothecin, gemcitabine, 5-fluouracil, rifampicin, tamoxifen, ellipticin, ethotrexate, daunomycin, estrogen, curcumin, and an siRNA, or any combination thereof. In some embodiments, the drug is a hydrophobic drug sequestered in the hydrophobic layer of the bilayer. In some embodiments, the drug is a hydrophilic drug encapsulated in the aqueous interior of the bilayer shell.

Also provided are methods of making a liposome comprising a lipid bilayer having a hydrophilic exterior surface and an aqueous interior and comprising at least one fusion polymer comprising (i) a tumor targeting domain that binds to exposed collagenous (XC) proteins, and (ii) a multi-block polymer comprising sequentially a first hydrophilic block, a first hydrophobic block, a second hydrophobic block, and a second hydrophilic block, wherein the tumor targeting domain of the at least one fusion polymer extends outwardly from the hydrophilic exterior surface of the liposome, such that the tumor targeting domain can bind to XC proteins while associated with the liposome. The method of making a liposome can comprise (a) providing a first and a second plurality of multi-block polymers, each comprising sequentially a first hydrophilic block, a first hydrophobic block, a second hydrophobic block, and a second hydrophilic block, wherein the multi-block polymers of the second plurality each comprise a linker bound to the terminus of the first hydrophilic block, and wherein a maleimide group is bound to the linker terminus that is unbound to the hydrophilic block; (b) mixing the first and second plurality of multi-block polymers to thereby form a liposome; (c) providing a tumor-targeting domain that binds to exposed collagenous proteins and that comprises a cysteine residue on a terminus of the domain; and (d) combining the liposome of (b) with the tumor-targeting domain of (c) under conditions such that an activated maleimide of the multi-block polymers of the second plurality in the liposome reacts with the cysteine residue of the tumor-targeting domain, thereby connecting the tumor-targeting domain and the liposome.

In some embodiments the method of making a liposome comprises: (a) providing a first and a second plurality of multi-block polymers, each comprising sequentially a first hydrophilic block, a first hydrophobic block, a second hydrophobic block, and a second hydrophilic block, wherein the multi-block polymers of the second plurality each comprise a linker bound to the terminus of the first hydrophilic block, and wherein a maleimide group is bound to the linker terminus that is unbound to the hydrophilic block; (b) providing a tumor-targeting domain that binds to exposed collagenous proteins and that comprises a cysteine residue on a terminus of the domain; (c) combining the second plurality of multi-block polymers of (a) with the tumor-targeting domain of (b) under conditions such that an activated maleimide of the multi-block polymers of the second plurality in the liposome reacts with the cysteine residue of the tumor-targeting domain, thereby connecting the tumor-targeting domain and the multi-block polymer and creating a fusion polymer; and (d) mixing the fusion polymer of (c) with the first plurality of multi-block polymers to thereby form a micelle.

In some embodiments, the method of making a liposome further comprises, during mixing, adding a therapeutic agent under conditions sufficient to form a liposome that encapsulates the therapeutic agent.

Also provided are methods of making a drug delivery nanoparticle comprising (1) a liposome comprising a lipid bilayer having a hydrophilic exterior surface and an aqueous interior and comprising at least one fusion polymer comprising (i) a tumor targeting domain that binds to exposed collagenous (XC) proteins, and (ii) a multi-block polymer comprising sequentially a first hydrophilic block, a first hydrophobic block, a second hydrophobic block, and a second hydrophilic block, wherein the tumor targeting domain of the at least one fusion polymer extends outwardly from the hydrophilic exterior surface of the liposome, such that the tumor targeting domain can bind to XC proteins while associated with the liposome and (2) a drug sequestered inside the aqueous interior of the liposome. The method of making a drug delivery nanoparticle comprises (a) providing the drug; (b) providing the liposome; and (c) mixing the drug and the liposome to allow association of the liposome with the drug, thereby forming a drug-delivery nanoparticle.

Provided herein are pharmaceutical compositions comprising any one of the fusion polymers described herein and a pharmaceutical acceptable carrier. Also provided herein are kits that include one or more of the fusion polymers described herein.

Also provided are methods of treating cancer in a subject that include, e.g., administering to the subject a pharmaceutically effective amount of a pharmaceutical composition described herein. The cancer can be a primary or metastatic cancer e.g., colorectal cancer, breast cancer, brain cancer, non-small cell lung cancer, pancreatic cancer, prostate cancer, a sarcoma, a carcinoma, or a melanoma. Also contemplated are treatments of multiple types of cancer, simultaneously, using one or more of the compositions described herein.

As used herein, the term "fusion protein" or "onco-aptamer" is a polypeptide containing portions of amino acid sequence derived from two or more different proteins, or two or more regions of the same protein that are not normally contiguous.

The term "aptamer" is art-known and refers to an oligonucleotide or polypeptide that binds to a specific target molecule with high affinity and specificity.

The terms "polypeptide" or "peptide" as used herein are intended to encompass any amino acid sequence and include modified sequences such as those modified via PEGylation or acetylation. A "polypeptide" can be recombinantly or synthetically synthesized.

The term "micelle" or "polymer micelle" is art-known and means a generally spherical nanoparticle structure of amphipathic molecules, or molecules that have a polar head and a nonpolar tail, wherein the nonpolar tails are generally inside the micelle and shielded from water by the polar heads that generally line the outside of the micelle.

The term "liposome" is art-known and means a nanoparticle made of polymers and having at least one closed membrane. The at least one closed membrane can comprise a single bilayer or may comprise two or more concentrically arranged bilayers and the closed membrane can define an internal aqueous compartment.

The term "collagen-binding domain" is known in the art and refers to any polypeptide, or portion thereof, that can bind collagen, e.g., the collagenous proteins that are newly expressed and/or exposed in injured tissues and invasive cancers, as well as collagenous affinity matrices prepared in vitro. Several collagen-binding domains are known in the art (Cruz M A, et al., J. Biol. Chem., 270:10822-10827, 1995; Hoylaerts, M. F., et al., Biochem. J., 324:185-191, 1997; Lankhof, H., et al., Thrombos Haemostas, 75:950-958, 1996, which are incorporated herein in their entirety).

The term "paclitaxel-binding domain" refers to any polypeptide, or portion thereof, that can bind paclitaxel. Several paclitaxel-binding domains have been described based on the suspected substrates that paclitaxel bind, including beta-tubulin (Rao et al., J. Biol. Chem., 1994, 269:3132-4; Rao et al., J. Biol. Chem., 1995, 270:20235-8; Amos and Lowe, Chem. & Biol. 1999, 6:R65-69); the anti-apoptotic protein Bcl-2 (Fang et al., Cancer Res., 1998, 89:3202-8; Rodi et al., J. Mol. Biol., 1999, 285:197-203); and the nuclear transcription factor NFX1 (Aoki et al., Bioconjugate Chem., 2007, 18:1981-6; Katzenellenbogen et al., J. Virol., 2007, 81:3786-96, which are incorporated herein in their entirety).

The term "immunoglobulin-binding domain" refers to any polypeptide, or portion thereof, that can bind immunoglobulin.

As used herein, the term "monoclonal antibody" refers to a population of antibody molecules that include only one species of an antigen binding site capable of immune-reacting with a particular epitope of a polypeptide or protein. A monoclonal antibody thus typically displays a single binding affinity for the protein to which it specifically binds.

The term "RNA-binding domain" refers to any polypeptide, or portion thereof, that can bind ribonucleic acid (RNA).

The term "human serum albumin-binding domain" or "HSA-binding domain" refers to a structure that comprises a thiol-reactive maleimide group or a polypeptide, or portion thereof, that can bind human serum albumin.

The term "treatment" refers to the administration of one or more pharmaceutical agents to a subject or the performance of a medical procedure on the body of a subject. The term treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" is an animal, e.g., a mammal. A specific example of a subject would be, e.g., a human, e.g., an adult human or juvenile. Veterinary applications are also contemplated and a subject can be, e.g., a monkey, dog, cat, horse, cow, pig, goat, rabbit, rat, or mouse.

An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 6A is a diagram illustrating targeting of paclitaxel by Taxol-Aptamers to subcutaneous tumors in nude mice and an image of the subcutaneous tumor in a nude mouse.

FIG. 6B is a panel of images that show Taxol-aptamer dependent tumor targeting of paclitaxel, shown here by the comparative fluorescence of excised tumors.

FIG. 6C is an image that shows that when used with Taxol-aptamer, paclitaxel exhibited anti-angiogenic activity (i.e., potential efficacy) at 0.2 mg/kg, only $\frac{1}{50}$th of the normal effective dose of paclitaxel used in mice (10 mg/kg).

FIG. 8A is a diagram showing the structures of two representative mAb-Tropins (M03 and P38).

FIG. 8B is an image that shows that the combined antibody-binding and collagen-binding activity of M03 is positive and peptide-dependent, while that of P38 is nearly negative.

FIG. 8C is a graph that shows that increasing the concentrations of the M03 mAb-Aptamer also increased the collagen-bound retentates of Avastin (a humanized mAb) in the XC-agarose columns.

FIG. 8D is an image that shows that increasing the concentrations of the M03 mAb-Aptamer also increased the collagen-bound retentates of Avastin (a humanized mAb) in the XC-agarose columns.

FIG. 9A is an image of VEGF-stimulated growth and proliferation of HUVEC cells in control columns (control medium eluate). Mitotic cells are identified by white arrows.

FIG. 9B is an image of VEGF-stimulated growth and proliferation of HUVEC cells in control columns (control medium eluate). Mitotic cells are identified by white arrows.

FIG. 9C is an image of VEGF-stimulated growth and proliferation of HUVEC cells in control columns (control medium eluate). Mitotic cells are identified by white arrows.

FIG. 9D is an image illustrating that the VEGF-stimulated growth and proliferation of the HUVEC cells was blocked in VEGF-Trap (collagen/mAb-Tropin/Avastin complex) columns, demonstrating that the collagen-bound Aptamer-Avastin complexes retained their biological activity.

FIG. 9E is an image illustrating that the VEGF-stimulated growth and proliferation of the HUVEC cells was blocked in VEGF-Trap (collagen/mAb-Tropin/Avastin complex) columns, demonstrating that the collagen-bound Aptamer-Avastin complexes retained their biological activity.

FIG. 9F is an image illustrating that the VEGF-stimulated growth and proliferation of the HUVEC cells was blocked in VEGF-Trap (collagen/mAb-Tropin/Avastin complex) columns, demonstrating that the collagen-bound Aptamer-Avastin complexes retained their biological activity.

FIG. 10A is a diagram showing the structures of two RNA-binding and collagen-binding fusion peptides (RNA-Apt 07 and RNA-Apt 08) that were generated and tested.

FIG. 10B is an image that shows that both RNA-Apt 07 and RNA-Apt 08 depleted fluorescently labeled-oligonucleotides from the column eluates.

FIG. 10C is an image that shows that both RNA-Apt 07 and RNA-Apt 08 retained the labeled oligonucleotides on the collagen-agarose mini-columns.

FIG. 11A is a panel of bright field and fluorescence images of a tumor excised from a mouse treated with intravenous (tail vein) infusions of IgG$^{FITC}$ minus the collagen-binding/IgG-binding fusion aptamer.

FIG. 11B is a panel of bright field and fluorescence images of a tumor excised from a mouse treated with intravenous (tail vein) infusions of IgG$^{FITC}$ plus the collagen-binding/IgG-binding fusion aptamer, demonstrating XC-binding domain-dependent tumor targeting of IgGs.

FIG. 11C is a panel of bright field and fluorescence images of a control tumor (untreated), used to determine the level of background auto-fluorescence.

FIG. 12 is an image illustrating a functional analysis, via comparative XC-column chromatography, of the maleimide-activated binding of multi-human serum albumin (HSA) tropins (Aptamer-3 and Aptamer-4) to the free cysteine-34 of recombinant HSA. The collagen-binding/albumin fusion polymers were detected using FITC-labeled goat anti-HSA antibodies.

FIG. 13 is a schematic of the novel tripartite onco-aptamer, CpBio-MA3TX, named TargaTaxel. This schematic shows the (i) maleimide-activated Albumin linkage; (ii) a proven collagen-binding/tumor-targeting domain; and (iii) a high efficiency Taxol-binding domain.

FIG. 14A is a schematic of an exemplary tumor-targeting bifunctional fusion nanoparticle system, illustrating the structure of a maleimide-activated di-block copolymer and a schematic of a bifunctional polymer formed by the linking of a tumor-targeted collagen-binding onco-aptamer and a maleimide-activated di-block copolymer.

FIG. 14B is a schematic of an exemplary bifunctional fusion nanoparticle tumor-targeting system, illustrating a drug loaded nano-micelle.

FIG. 14C is a schematic of an exemplary bifunctional fusion nanoparticle tumor-targeting system, illustrating a drug delivery nanoparticle created with tumor-targeted polymers of the present invention.

FIG. 15A is a schematic of two tumor-targeted collagen-binding peptides.

FIG. 15B is an image of an XC-agarose chromatography analysis of polymeric micelles loaded with Courmarin-6 and coupled to the tumor-targeting peptides from FIG. 15A.

FIG. 15C is a graph of the quantification of the column eluates of FIG. 15B, confirming that Aptamer 1 (N-terminal Cys) demonstrates greater coupling efficiency.

FIG. 16A is a bright field image illustrating selectivity of a Taxol-Tropin fusion polymer for the XC proteins of a collagen-agarose matrix. The aptamer-dependent (Tx-Aptamer 2 from FIG. 4A) binding of fluorescent paclitaxel (Taxol-green) to the XC-agarose layer is demonstrated by column chromatography.

FIG. 16B is a blue-light/amber filter trans-illumination image illustrating selectivity of a Taxol-Tropin fusion polymer for the XC proteins of a collagen-agarose matrix. The aptamer-dependent (Tx-Aptamer 2 from FIG. 4A) binding of fluorescent paclitaxel (Taxol-green) to the XC-agarose layer is demonstrated by column chromatography.

DETAILED DESCRIPTION

The present disclosure is based, at least in part, on the development of new bifunctional fusion polymers that include at least two functional domains: (i) sequences that bind to the Exposed Collagenous (XC-) proteins present in pathological areas such as cancerous lesions, and (ii) sequences that bind directly or indirectly to a particular class of chemotherapeutic or biologic agents, for example, paclitaxel, monoclonal antibodies, growth factors, or small interfering RNA (siRNA). The present disclosure is also based, at least in part, on the development of new bifunctional fusion nanoparticles that include at least two functional portions: (i) a least one fusion polymer that includes a sequence that binds to Exposed Collagenous (XC-) proteins, and an amphiphilic polymer with distinct hydrophobic and hydrophilic block domains that self-assemble with similar polymers to assemble a core-shell structure, and (ii) a nanoparticle that non-covalently sequesters chemotherapeutic or biologic agents, for example agents with hydrophobic or hydrophilic characteristics or nucleic acids. The bifunctional properties of these engineered fusion polymers and nanoparticles may enable selective and efficient targeting of the widely used chemotherapeutic and biologic agents to abnormal, diseased, or degenerative tissues such as tumors, allowing lower doses of these agents to become more effective at killing cancer cells and associated blood supply. Targeting is achieved by combining a tumor-targeting functional domain with a high-affinity, non-covalent drug-binding domain of the fusion polymers or with drug-delivery nanoparticle, generating drug complexes with improved biodistribution. Targeted delivery of drugs using the fusion peptide and nanoparticles disclosed herein can reduce systemic toxicity and side effects by sequestering the drugs in the tumor microenvironment and sparing normal cells and tissues from the toxicity of the drugs. Moreover, by targeting a common histopathologic property of primary tumors and metastatic lesions, the drug delivery systems described herein can (i) bind and carry one or more FDA-approved therapeutic drugs, in some instances upon simple mixing, and (ii) seek out and accumulate in the diseased/cancerous tissues following intravenous infusion. Thus, the fusion polymers and nanoparticles described herein may make conventional chemotherapeutic and biologic agents more efficient with great efficacy while lessening unwanted side effects, improving the overall Therapeutic Index and patient survival. These fusion polymers and nanoparticles can also include linker segments and/or flanking sequences to improve the functionality, pharmacokinetics, stability, and/or pharmacodynamics of the targeted drug delivery.

Selective Targeting of Therapeutic Agents to Tumor Microenvironment

Figure 1B:
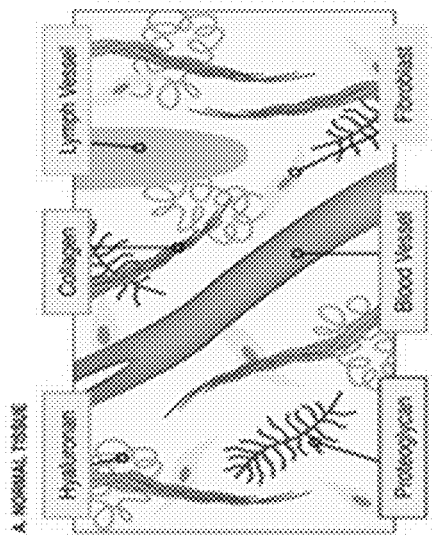
FIG. 1B is a diagram illustrating the histology of tumor tissue and shows that tumor invasion, metastasis, angiogenesis, and reactive stroma formation result in the disruption of the normal histology and the pathologic exposure of collagenous XC-proteins within the tumor microenvironment.
Figure 1A:
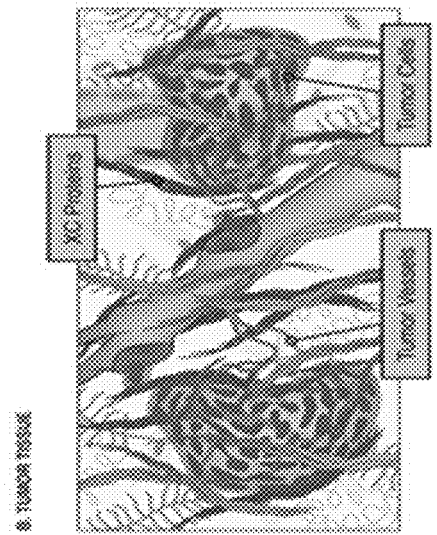
FIG. 1A is a diagram illustrating the histology of normal tissue and shows that in normal, uninjured tissues, collagen is not exposed to the general circulation.

Neoplastic lesions do not only comprise malignant cancer cells but also include stromal components such as fibroblasts, endothelial cells, and inflammatory cells. An opportunistic tumor microenvironment is formed by those components and promotes tumorigenesis, tumor progression and metastasis. Although cancer drug development traditionally focused on targeting the cancer cell and its cell division cycle, emphasis has recently shifted toward the tumor microenvironment for novel therapeutic and prevention strategies (See Sounni and Noel, Clinical Chem., 59:85-93, 2013; Fang and DeClerck, Cancer Res., 73:4965-4977, 2013). As shown in FIG. 1, the process of tumor invasion, metastasis, angiogenesis, and reactive stroma formation disrupts normal tissue histology and leads to pathologic exposure of collagenous proteins (XC-) within the tumor microenvironment. Thus, the abnormal exposure of collagenous proteins is a characteristic histopathologic property of all neoplastic lesions.

"Pathotropic (disease-seeking) Targeting" of drugs to cancerous tissues utilizes the pathology of tumor itself (XC-protein expression) as the biochemical target, rather than the unique, varied, rapidly evolving cancer cells per se. By targeting a common histopathologic property of primary tumors and metastatic lesions, the drug delivery systems described herein can (i) bind and carry a well-characterized (e.g., FDA-approved) therapeutic drug, upon simple mixing, and (ii) seek-out and accumulate in the diseased/cancerous tissues upon intravenous infusion. The advent of Pathotropic Targeting ushered the field of genetic medicine into the clinic (Waehler et al., Nature Reviews Genetics 8:573-587, 2007). Further advancement of the field of targeted antitumor therapy was made with the development of Rexin-G (Hall et al., Hum Gene Ther 11:983-993, 2000; Gordon et al., Cancer Res. 60:3343-3347, 2000; Hall et al., Intl J Mol Med 6:635-643, 2000)—a nanoparticle gene delivery system which incorporates a physiological surveillance function inherent in the primary structure of von Willebrand Factor—to enable a specific gain-of-function that is highly selective for the pathologic stroma that is characteristic of neoplastic lesions (Gordon et al., Cancer Res. 60:3343-3347, 2000). Indeed, the clinical administration of this tumor-targeted Rexin-G vector has been shown to accumulate in primary and metastatic lesions, resulting in enhanced cytotoxic gene delivery, and thus enhanced clinical efficacy (Gordon et al., Expert Opin Biol Ther 10:819-832, 2010; Gordon et al., Int'l J Oncol 36:1341-1353, 2010; Chawla et al., Mol Ther 2009; 17(9):1651-7; Chawla et al., Mol Ther 2010; 18:435-441).

To avoid the problems caused by traditional chemotherapeutic regimens, a modality of drug administration called "metronomic chemotherapy" has been proposed, which refers to the chronic, equally spaced administration of low doses of various chemotherapeutic drugs without extended rest periods. Metronomic chemotherapy targets endothelial cells rather than tumor cells.

Provided herein are novel bifunctional fusion polymers (also called "onco-aptamers") that target pharmaceutical agents to pathological areas. The fusion polymers described herein contain two or more domains: (i) sequences that bind to Exposed Collagenous (XC-) proteins present in pathological areas, including cancerous lesions, and (ii) sequences that bind to specific pharmaceutical agents (see FIG. 2A). These fusion polymers can also include (iii) linker segments and/or (iv) flanking sequences to improve the functionality, pharmacokinetics, stability, and/or pharmacodynamics of the targeted drug delivery (see FIG. 2B). Also provided herein are novel bifunctional fusion nanoparticles for targeting pharmaceutical agents to pathological areas. The fusion nanoparticles can include two or more portions: (i) at least one fusion polymer that includes a sequence that binds to Exposed Collagenous (XC-) proteins present in pathological areas, such as cancerous lesions, and an amphiphilic polymer with distinct hydrophobic and hydrophilic block domains that self-assemble with similar polymers to assemble a core-shell structure, and (ii) a nanoparticle that covalently sequesters chemotherapeutic or biologic agents (e.g., FIG. 14A). These fusion polymers can also include (iii) linker segments and/or (iv) flanking sequences to improve the functionality, pharmacokinetics, stability, and/or pharmacodynamics of the targeted drug delivery (e.g., FIG. 14A).

The molecular engineering of these bifunctional polymers and nanoparticles creates a two-handed structure with at least two distinct binding domains separated by flexible linkers or spacers—to avoid steric hindrances between the functional domains. These fusion polymers and nanoparticles enable tumor-targeted delivery of the chemotherapeutic and biologic agents, e.g., anticancer agents.

The drug-binding properties of these fusion polymers and nanoparticles are based on high-affinity, non-covalent interactions, which do not substantially alter the chemical composition or the commercial manufacturing of the pharmaceutical agents. The complete elimination of the bioactive therapeutic agent from the primary structure of these targeting fusion polymers greatly reduces the overall size of the constructs to less than 50 amino acids (~5 kDa), which is thereby amenable to GMP production by chemical synthesis, avoiding the production and purification methodologies required for larger proteins prepared from biologic sources that are associated with a myriad of medical, pharmacological, and regulatory concerns. The chemical structure and pharmaceutical purity of these newly-developed tumor targeting fusion polymers and nanoparticles are readily verifiable—by virtue of the synthetic chemistries involved. Furthermore, the chemical composition and commercial manufacture of the bioactive pharmaceutical agents to be delivered by these targeting peptides and nanoparticles are not substantially altered due to the non-covalent binding.

The fusion polymers and nanoparticles described herein have a collagen-binding domain. In some embodiments, the collagen-binding domain is derived from a collagen-binding domain of von Willebrand factor, which is involved in the recognition of exposed vascular collagen (Takagi, J., et al., Biochemistry 32:8530-4, 1992; Tuan, T. L., et al., Conn. Tiss. Res. 34:1-9, 1996; Gordon, E. M., et al., Hum. Gene Ther. 8:1385-1394; U.S. Pat. No. 6,387,663, all herein incorporated by reference). von Willebrand factor was initially identified as a hemostatic factor in studies of inherited hemophilias (Wagner, Ann. Rev. Cell. Biol. 6:217, 1990), and has been shown to perform a vital surveillance function by targeting platelet aggregates to injured/diseased tissues and vascular lesions (Ginsburg and Bowie, Blood 79:2507-2519, 1992).

In some embodiments, the collagen-binding domain comprises an amino acid sequence of SEQ ID NO: 1 or SEQ ID NO: 2 or both. Skilled practitioners will appreciate that variations in these sequences are possible and such variants may be useful in the present invention. Accordingly, sequences having at least 70%, e.g., at least 80%, 90%, or at least 99% identity to SEQ ID NO.: 1 or SEQ ID NO.: 2 can be utilized.

Tumor-Targeting and Paclitaxel-Binding Fusion Polymers (Taxol-Tropins)

The taxanes are a group of drugs that includes paclitaxel (Taxol®) and docetaxel (Taxotere®) that exhibit antitumor activity against a wide range of human cancers by binding to and stabilizing microtubules. Since microtubules are essential to cell division, taxane-binding and stabilization of microtubules inhibits cell division and disrupts cell cycle. The efficacy of taxane-based therapy is often limited by systemic toxicity, which results in poor therapeutic index. The systemic toxicity of taxanes is due to their non-selective cytotoxicity toward tumor cells versus normal cells. This indiscriminate property results in severe side effects, including bone marrow suppression, febrile neutropenia, neurotoxicity, mucositis, ulceration of the mouth and throat, as well as a variety of cardiac abnormalities. This untoward toxicity of taxane-based therapy has restricted the administration and dose levels, which often lead to incomplete tumor eradication.

One way to reduce the side effects of taxanes is to directly target taxanes to the primary and metastatic tumor sites. Such selective tumor targeting can increase the bioavailability of the drug within the tumors. Albumin drug complexes can reach tumors passively to some extent through the leaky vasculature surrounding the tumors by the Enhanced Permeability and Retention (EPR) effect. However, recent studies performed in a directly comparative manner have had a sobering effect: the results of a recent NCI-sponsored Phase III breast cancer trial comparing paclitaxel with albumin-based nab-paclitaxel (Abraxane) determined that i.v. paclitaxel (Taxol) performed just as good or better than Abraxane, with significantly less toxicity (Rugo et al., 2015 *Randomized Phase III Trial of Paclitaxel Once Per Week Compared With Nanoparticle Albumin-Bound Nab Paclitaxel Once Per Week or Ixabepilone With Bevacizumab as First-Line Chemotherapy for Locally Recurrent or Metastatic Breast Cancer: CALGB 40502/NCCTG N063H (Alliance).*, J. Clinical Oncology, 33:2361-2369). Drugs such as Taxol and Abraxane (which are administered at necessarily high (equi-toxic) doses) could be further improved by active targeting. The use of active targeting technology could enable lower (not higher) doses of taxanes to become more clinically effective.

In some embodiments, the fusion polymers described herein comprise a collagen-binding domain and a paclitaxel-binding domain. These fusion polymers can directly bind to paclitaxel and target paclitaxel to neoplastic lesions. In some embodiments, the paclitaxel-binding domain of the fusion polymers is derived from a paclitaxel-binding domain of NFX1. For example, the paclitaxel-binding domain can comprise an amino acid sequence selected from the group consisting of: SEQ ID NO: 3, SEQ ID NO: 4, SEQ ID NO: 5, and SEQ ID NO: 6. Skilled practitioners will appreciate that variations in such sequences may be possible, while retaining paclitaxel-binding activity. Accordingly, sequences having at least 70%, e.g., at least 80%, 90%, 95%, or at least 99%, identity to SEQ ID NO: 3, SEQ ID NO: 4, SEQ ID NO: 5, and SEQ ID NO: 6, can be utilized.

In some embodiments, the tumor-targeting and paclitaxel-binding fusion polymers further include one or more linkers/spacers. These linkers/spacers can add flexibility, reducing the steric hindrances between the functional binding domains. The tumor-targeting and paclitaxel-binding fusion polymers can have one or more linkers comprising an amino acid sequence such as SEQ ID NO: 7, SEQ ID NO: 8, SEQ ID NO: 9, or SEQ ID NO: 10, or variants of these sequences. In some embodiments, the fusion polymer can be acetylated, amidated, and/or PEGylated at N- or C-terminus. Alternatively or in addition, D-amino acids can be included. Inclusion of D-amino acids, acetylation, amidation, and/or PEGylation increase the stability of the fusion polymers and make them more resistant to proteolysis.

Exemplary amino acid sequences of tumor-targeting and paclitaxel-binding fusion polymers include SEQ ID NO: 11, SEQ ID NO: 12, SEQ ID NO: 13 and SEQ ID NO: 14. Skilled practitioners will appreciate that variations in such sequences may be possible, while retaining tumor- and paclitaxel-binding activity. Accordingly, sequences having at least 70%, e.g., at least 80%, 90%, 95%, or at least 99%, identity to SEQ ID NO: 11, SEQ ID NO: 12, SEQ ID NO: 13, or SEQ ID NO: 14, can be utilized.

Tumor-Targeting and Monoclonal Antibody (mAb)-Binding Fusion Polymers (mAb-Tropins)

The use of monoclonal antibodies (mAbs) for cancer therapy has achieved considerable success in recent years. In a relatively short period of time, mAbs have entered the mainstream of anticancer therapy. Monoclonal antibodies were first used as antagonists of oncogenic receptor tyrosine kinases, but today mAbs have emerged both as vehicles for the targeted delivery of potent chemotherapeutic agents and as powerful tools to manipulate tumor angiogenesis and anti-tumor immune responses. With ever more promising results from the clinic, the future will likely see continued growth in the discovery and development of therapeutic antibodies.

Figure 2A:
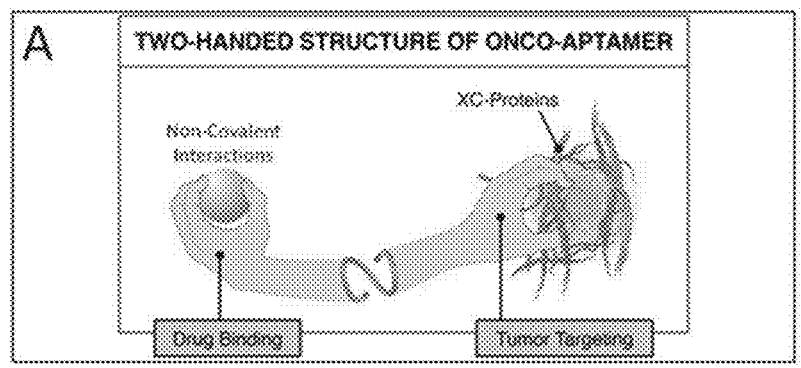
FIG. 2A is a diagram illustrating the two-handed structure of the bifunctional fusion polymers. The fusion polymers contain two primary binding elements: (1) a XC-binding domain (tumor-targeting domain) and (2) a drug-binding domain.
Figure 2B:
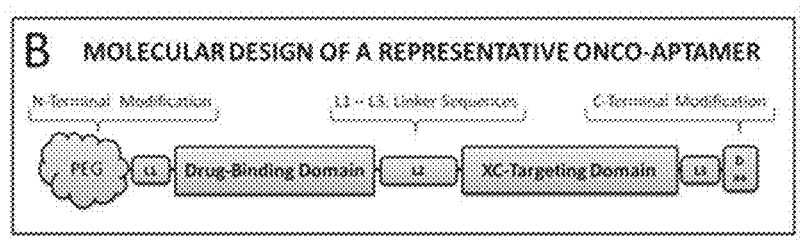
FIG. 2B is a diagram illustrating the molecular design of a representative fusion polymer (onco-aptamer) with a XC-binding tumor-targeting domain and a drug binding domain.
Figure 2C:
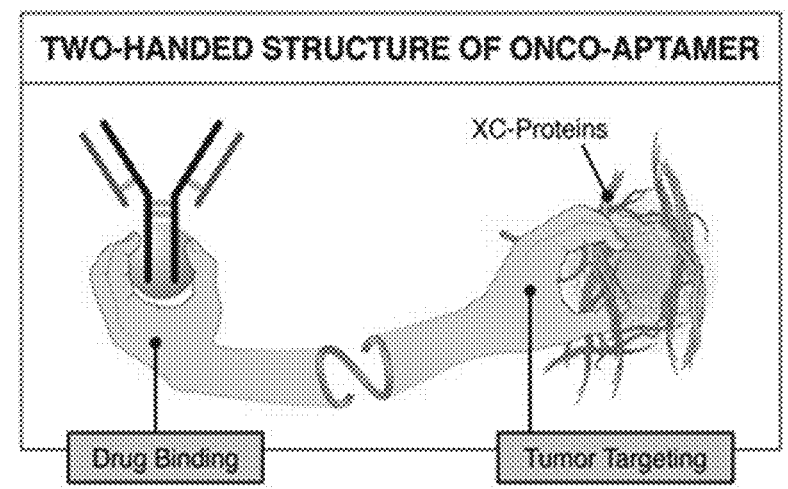
FIG. 2C is a diagram illustrating the two-handed structure of the bifunctional fusion polymers. The fusion polymer demonstrated here contains two primary elements: (1) and XC-binding domain (tumor-targeting domain) and (2) a drug-binding domain that can bind IgGs.
Figure 2D:
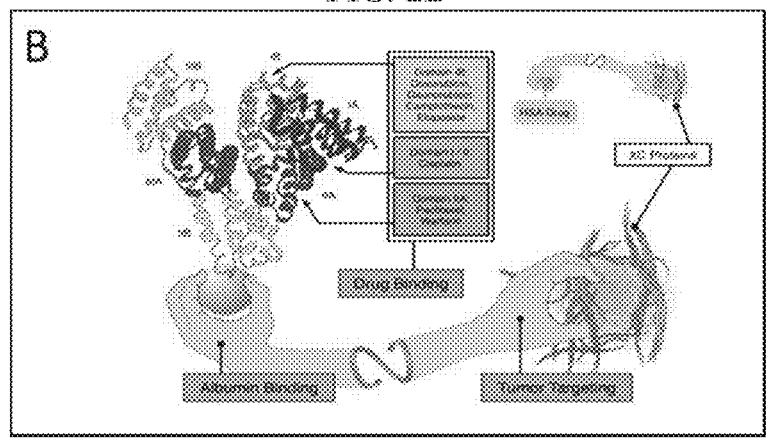
FIG. 2D is a diagram illustrating targeted drug delivery using Human Serum Albumin (HSA)-aptamer fusions. In this tumor-targeting HSA-binding system, many therapeutic agents bind tightly to albumin, and this interaction can increase the half-life of the therapeutic agent in circulation.

In some embodiments, the fusion polymers described herein comprise a collagen-binding domain and an immunoglobulin-binding domain (FIG. 2A). These fusion polymers can directly bind to immunoglobulins such as monoclonal antibodies and target them to neoplastic lesions. A minimal IgG-binding domain of 35 amino-acids, corresponding to an N-terminal domain of the fibrinogen-binding protein FgBP, was previously reported (Meehan et al., Microbiology, 2001, 147:3311-22; 2009, 155:2583-92). The tethering of mAbs to a synthetic fragment of the deduced IgG-binding domain of FgBP, as well as IgG-binding peptide sequences determined by bio-panning (DeLano et al., 2000, Science, 287:1279-83; Yang et al., J. Peptide Res., 66: 120-137; 2005), are amenable to target mAb to tumors.

In some embodiments, the immunoglobulin-binding domain of the fusion polymers comprises the hexamer sequence of SEQ ID NO: 15, which has been shown to bind to the Fc region of human, bovine, mouse, goat, and rabbit immunoglobulins (IgGs)—(Yang et al., J. Chromatography, 2009, 1216:910-18; Yang et al., J. Mol. Recognition, 2010, 23:271-82, which are incorporated herein in their entirety). Skilled practitioners will appreciate that the sequence of SEQ ID NO:15 could be modified and tested to modify or retain at least some portion of its Fc binding activity and, accordingly, variants (i.e., sequences with at least 70%, e.g., at least 80% or at least 90% identity to SEQ ID NO: 15) can be useful in certain embodiments.

In some embodiments, the tumor-targeting and immunoglobulin-binding fusion polymers further include one or more linkers/spacers, to reduce the steric hindrances between the functional binding domains. The tumor-targeting and immunoglobulin-binding fusion polymers can have one or more linkers comprising an amino acid sequence selected from the group consisting of SEQ ID NO: 16, SEQ ID NO: 17, SEQ ID NO: 8, SEQ ID NO: 9, SEQ ID NO: 57, and SEQ ID NO: 58, or variants of these sequences. In some embodiments, the fusion polymers can be acetylated, amidated, and/or PEGylated at N- or C-terminus. Alternatively or in addition, D-amino acids can be included. Inclusion of D-amino acids, acetylation, amidation, and/or PEGylation can increase the stability of the fusion polymers and can make them more resistant to proteolysis.

Exemplary amino acid sequences of tumor-targeting and immunoglobulin-binding fusion polymers include SEQ ID NO: 18, SEQ ID NO: 19, SEQ ID NO: 20 and SEQ ID NO: 21. Skilled practitioners will appreciate that variations in such sequences may be possible, while retaining tumor- and immunoglobulin-binding activity. Accordingly, sequences having at least 70%, e.g., at least 80%, 90%, 95%, or at least 99%, identity to SEQ ID NO: 18, SEQ ID NO: 19, SEQ ID NO: 20 or SEQ ID NO: 21, can be utilized.

In some embodiments, the immunoglobulin-binding domain described herein can bind monoclonal antibodies such as immune checkpoint inhibitors, thereby serving to restrict antibody-mediated immune activation to tumor compartments. Exemplary immune or T-cell checkpoint inhibitors include anti-cytotoxic T lymphocyte antigen-4 (CTLA-4), anti-programmed death-1 (anti-PD-1) and anti-PD-ligand-1 (anti-PD-L1) monoclonal antibodies. The use of T-cell checkpoint inhibitors for breaking immune tolerance is a major advancement in cancer immunology. Under normal physiological conditions PD-L1 binds to the transmembrane PD-1 on an immune cell surface and inhibits the immune activity of the cell. Cancer cells can upregulate PD-L1 so as to inhibit the T-cells that might otherwise attack the tumor cells. Antibodies such as anti-PD-1 mAbs block the interaction between PD-L1 and PD-1, activating the immune system of the T-cell so that it can attack the tumor. Similarly CTLA-4 is an antibody expressed on the surface of T-cells that transmits inhibitory signal in the T-cell. This inhibitory signal can be blocked with anti-CTLA-4 antibodies, such that the immune system can recognize and target cancer cells.

The use of anti-CTLA-4, anti-PD-1 or PD-L1 antibodies is associated with a wide range of side effects known as immune-related adverse events (irAEs), which can impact dermatologic, gastrointestinal, hepatic, endocrine, and other organ systems, requiring subsequent immunosuppression with corticosteroids, tumor necrosis factor-alpha antagonists, mycophenolate mofetil, or other agents (Kong and Flynn, 2014; Chen et al., 2015; Postow et al., 2015). Thus, the therapeutic performance of such monoclonal antibodies can be enhanced by active tumor-targeting: thereby increasing the efficacy of the treatments within the tumor compartments while decreasing the autoimmune disorders and untoward inflammatory sequelae caused by the bioactivity of these checkpoint inhibitors in non-target organs.

These immune checkpoint inhibiting fusion polymers can comprise the full length mAb or a functional fragment thereof, and can further include the linkers/spacers and N-terminal/C-terminal shielding as described herein. Accordingly, included herein are methods of treating a disease, for example, cancer. The cancer can be, e.g., a primary or metastatic cancer, including but not restricted to, colorectal cancer, breast cancer, brain tumors, non-small cell lung cancer, pancreatic cancer, prostate cancer, sarcoma, carcinoma, and/or melanoma. The cancer can be, e.g., cancer of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and/or throat; sarcoma, or choriocarcinoma. In general, the methods of treating cancer can include administering to a subject having cancer an amount of the immune-checkpoint inhibiting fusion polymer or pharmaceutical composition sufficient to treat cancer in the patient. The use of a tumor-targeted XC polymer fused with immune checkpoint inhibitors can compartmentalize the T-cell response in the tumor microenvironment (TME), increase the efficacy of T cell response locally in the TME, and reduce the severity of systemic immune-mediated adverse events.

Tumor-Targeting and RNA-Binding Fusion Polymers (RNA-Tropins)

RNA interference (RNAi) using small interfering RNA sequences (siRNA) is one of the well-established strategies for gene silencing and cancer therapy (Burnett and Rossi, Cell, 19:60-71, 2012; Esposito et al., J. RNA Silencing, 10:500-506, 2014). To utilize RNAi for gene therapy applications, however, an efficient and safe method for delivering the therapeutic RNA molecules to the diseased tissues is both necessary and challenging (Bae and Park, J. Controlled Release, 153:198-205, 2011; Ling et al., Nature Reviews Drug Discovery, 12:847-855, 2013). To improve targeting specificity, the RNA delivery vehicles and/or vectors must be functionalized or chemically modified (Copolovici et al., ACS Nano, 8:1972-1994, 2014). In terms of cellular delivery and internalization, the plasma membrane is the primary, and most difficult, barrier for RNA to cross, because negatively charged RNA is strongly repulsed by the negatively charged cellular membrane. A variety of cationic polymers can be used as RNA carriers by interacting with RNA and covering its negative charges to form a cell-penetrating nanoparticle complex (Munyendo et al., Biomolecules, 2:187-202, 2012). Cationic cell-penetrating peptides (CPPs) are promising candidates for RNA carriers since they can cross the plasma membrane and be internalized into cells together with the "cargo" RNA (Bechara and Sagan, FEBS Letters, 587:1693-1702, 2013).

CPPs are short chains of amino acids with the distinct ability to cross cell plasma membranes. They are usually between seven and thirty residues in length. The commonality between all known CPPs is the presence of positively charged residues within the amino acid chain. Polyarginine and the transactivator of transcription (TAT) peptide are two widely used CPPs (Futaki et al., J. Biol. Chem. 2001, 276:5836-5840; Schmidt et al., FEBS Letters, 2010, 584: 1806-13). One advantage of CPPs is the ability to enhance the therapeutic delivery of a wide range of large-cargo molecules, such as oligonucleotides, into target cells (Zorko and Langel, Adv. Drug Delivery Rev., 57:529-545, 2004).

In some embodiments, the fusion polymers described herein comprise a collagen-binding domain and a RNA-binding domain. These fusion peptides can directly bind to siRNA and target them to neoplastic lesions. In some embodiments, the RNA-binding domain of the fusion polymers comprises CPPs such as polyarginine or the TAT peptide. In some embodiments, the RNA-binding domain comprises polyarginine SEQ ID NO: 29 or SEQ ID NO: 30.

In some embodiments, the tumor-targeting and RNA-binding fusion polymers further include one or more linkers/spacers, to reduce the steric hindrances between the functional binding domains. The tumor-targeting and RNA-binding fusion polymers can have one or more linkers comprising an amino acid sequence selected from the group consisting of SEQ ID NO: 31, SEQ ID NO: 32, SEQ ID NO: 8, SEQ ID NO: 58, SEQ ID NO: 33 and SEQ ID NO: 34, or variants of these sequences. In some embodiments, the fusion polymers are amidated, acetylated and/or PEGylated at N- or C-terminus. Inclusion of D-amino acids, amidation, acetylation, and/or PEGylation increase the stability of the fusion polymers and make them more resistant to proteolysis.

Exemplary amino acid sequences of tumor-targeting and RNA-binding fusion polymers include: SEQ ID NO: 35, SEQ ID NO: 36, SEQ ID NO: 37, SEQ ID NO: 38, and SEQ ID NO: 55. Skilled practitioners will appreciate that variations in such sequences may be possible, while retaining tumor- and RNA-binding activity. Accordingly, sequences having at least 70%, e.g., at least 80%, 90%, 95%, or at least 99%, identity to SEQ ID NO: 35, SEQ ID NO: 36, SEQ ID NO: 37, SEQ ID NO: 38, or SEQ ID NO.: 55 can be utilized.

Tumor-Targeting and Albumin-Binding Fusion Polymers (Multi-Tropins)

Albumin, a versatile protein carrier for drug delivery, has been shown to be nontoxic, non-immunogenic, biocompatible, and biodegradable. Albumin-mediated drug delivery systems have gained considerable attention owing to their high binding capacity of various drugs, and the tendency of good tolerance and less side-effects. Albumin was used to fabricate various nanoparticles and targeting vehicles for improving the therapeutic delivery of many drugs (Kratz, J. Controlled Release, 2008, 132:171-83; Kinam Park, J. Controlled. Release, 2012, 157:3; Kwon et al., J. Controlled Release, 2012, 164:108-14). Human serum albumin (HSA) can bind and transport copper (Quinlan et al., Hepatology, 41:1211-1219, 2005), including copper-based radiopharmaceuticals and PET imaging tracers (Lux et al., Theranostics, 5:277-288, 2015).

In 1986, Hiroshi Maeda intravenously injected the albumin-binding dye Evans Blue into mice bearing subcutaneous tumors and found that the Evans blue-albumin complexes accumulated discernibly within the tumors. This phenomenon of enhanced permeability and retention—in relation to passive tumor targeting—is largely a result of the abnormal endothelial cell organization and the large fenestrations of tumor vasculature that make the tumor tissue more permeable for albumin. Due to its passive entry into tumors via the enhanced permeability of tumor vasculature and a retention effect caused by increased demand for albumin by tumor cells as a source of energy and amino acids, albumin-based drug delivery systems have been shown to be useful for achieving improved cancer chemotherapy. The delivery of insoluble taxanes, for example, has been improved by the use of lipid-based solvents and albumin as a vehicle. The most popular formulation of albumin-bound paclitaxel (i.e., Abraxane) facilitates the infusion of this biocompatible vehicle, improves the tolerability, and lessens side effects; although enhanced efficacy is generally seen with higher, not lower, drug doses (Miele et al., Int. Journal of Nanomedicine, 2009, 4:91-97). Moreover, the U.S. FDA has made it clear that the passive tumor targeting by albumin does not provide the selectivity required for specific tumor-targeting although it may improve the solubility and/or the clinical dosing of drugs (Department of Health & Human Services, NDA #021660 Abraxane® for Injectable Suspension. Reference ID: 3063889).

The major problem with the passive targeting of albumin-drug complexes to tumors is the fact that there is upwards of 35 to 50 grams of normal serum albumin in a single liter of human blood—that amounts to 175 to 250 grams—which effectively competes with the milligram quantities of the drug and albumin components of these simplistic formulations. Therefore, active targeting must, necessarily, be several orders of magnitude higher in the affinity for tumor constituents to be truly effective. Integrin-binding Cyclic RGD peptides and their derivatives have been intensively studied as highly selective tumor targeting probes; however, the rather short blood circulation half-lives, greatly compromises their targeting efficacy. To address this issue, a cyclic RGD peptide and an organic dye were covalently conjugated onto human serum albumin (HSA), and these conjugates were subjected to fluorescence imaging and histologic analysis, which confirmed the enhanced performance in vivo (Chen et al., Mol. Imaging, 2009, 8:65-73). The success of this approach can be extended to other peptide-based probes and drugs that are physically conjugated with HSA for prolonged tumor penetration and improved pharmacokinetics.

In some embodiments, the fusion polymers described herein comprise a collagen-binding domain and an HSA-binding domain. These fusion peptides can directly bind to human serum albumin, which can in turn bind to a variety of therapeutic/biologic agent, and target the therapeutic/biologic agent bound by HSA to neoplastic lesions. In some embodiments, the fusion polymers bind human serum albumin in a non-covalent manner (see Albumin-Aptamer 1 and 2 of FIG. 2E). For example, the HSA-binding domain can have the amino acid sequence of SEQ ID NO: 39, or SEQ ID NO: 40, or variants of these sequences. Skilled practitioners will appreciate that the sequence of SEQ ID NO: 39 or SEQ ID NO: 40 could be modified and tested to modify or retain at least some portion of its Fc binding activity and, accordingly, variants (i.e., sequences with at least 70%, e.g., at least 80% or at least 90% identity to SEQ ID NO:15) can be useful in certain embodiments.

Figure 2E:
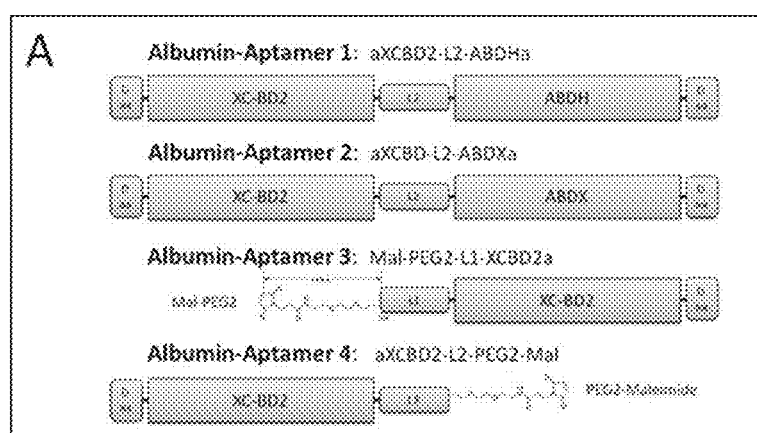
FIG. 2E is a diagram illustrating different embodiments of XC-binding HSA binding fusion polymers used for the tumor-targeted delivery of therapeutic agents bound to HSA.

In some embodiments, the fusion polymers bind human serum albumin contain a thiol-reactive maleimide group, which is capable of binding covalently to the single free cysteine residue (Cys-34) of human serum albumin (see Albumin-Aptamer 3 and 4 of FIG. 2E).

In some embodiments, the tumor-targeting and HSA-binding fusion polymers further include one or more linkers/spacers, to reduce the steric hindrances between the functional binding domains. The tumor-targeting and HSA-binding fusion polymers can have one or more linkers comprising an amino acid sequence selected from the group consisting of SEQ ID NO: 31, and SEQ ID NO: 9. In some embodiments, the fusion polymers are acetylated, amidated and/or PEGylated at N- or C-terminus. Inclusion of D-amino acids, acetylation, amidation, and/or PEGylation increase the stability of the fusion polymers and make them more resistant to proteolysis.

Exemplary amino acid sequences of tumor-targeting and HSA-binding fusion polymers include SEQ ID NO: 41, SEQ ID NO: 42, SEQ ID NO: 43, and SEQ ID NO: 44. Skilled practitioners will appreciate that variations in such sequences may be possible, while retaining tumor- and HSA-binding activity. Accordingly, sequences having at least 70%, e.g., at least 80%, 90%, 95%, or at least 99%, identity to SEQ ID NO: 41, SEQ ID NO: 42, SEQ ID NO: 43, or SEQ ID NO: 44, can be utilized.

Tumor-Targeting and Paclitaxel-Binding Fusion Polymers with N-terminal or C-Terminal Shielding In addition to the collagen-binding and drug-binding domains described above, fusion polymers can be further modified to include a shielding group on the terminus of the polymer. Non-limiting examples of these N- and C-terminal modifications are the addition of a PEG (poly(ethylene glycol)) moiety or a maleimide group to link covalently with albumin via human serum albumin (HSA) Cys-34. Both of these additions may shield the peptide from degradation, increase the stealth of the peptide and therefore may improve the circulating half-life of the peptides. The covalent tethering of HSA may serve to resist proteolytic degradation by serum proteases and additionally may reduce filtration of the targeting polymer by the kidneys. The addition of a maleimide group enables site-specific covalent coupling of the thiol-reactive group with a free cysteine residue, wherein, for example, the free cysteine residue could be that of the albumin protein or attached to the end of an aptamer to allow for site-specific covalent linking. Additional C-terminal modifications include protease-resistant "caps". These caps are D-amino acid substituted "caps" on the terminus of the polymer that may inhibit proteolysis of the aptamers by amino-peptidases and carboxypeptidases present in serum. These D-amino acid substituted "caps" are denoted herein by three letter coded amino acids in the lower case or by "D-" followed by the three letter amino acid code.

In some embodiments, the fusion polymers bind human serum albumin in a non-covalent manner (see Albumin-Aptamer 1 and 2 of FIG. 2E). For example, the HSA-binding domain can have the amino acid sequence of SEQ ID NO: 39, SEQ ID NO: 40, or variants of these sequences. In some embodiments, the fusion polymers include a thiol-reactive maleimide group, which is capable of binding covalently to the single free cysteine residue (Cys-34) of human serum albumin (see Albumin-Aptamer 3 and 4 of FIG. 2E).

In some embodiments, the tumor-targeting, paclitaxel-binding, and HSA-binding fusion polymers further include one or more linkers/spacers, to reduce the steric hindrances between the functional binding domains. The fusion polymers can have one or more linkers comprising an amino acid sequence selected from the group consisting of SEQ ID NO: 31, and SEQ ID NO: 9. In some embodiments, the fusion polymers are acetylated, amidated and/or PEGylated at N- or C-terminus. Additionally, the inclusion of D-amino acids can increase the stability of the fusion polymers and make them more resistant to proteolysis.

An exemplary amino acid sequence of a tumor-targeting, paclitaxel-binding, and PEG-shielded fusion polymer includes SEQ ID NO: 27. Skilled practitioners will appreciate that variations in such sequences may be possible, while retaining tumor- and paclitaxel-binding and PEG-shielded activity. Accordingly, sequences having at least 70%, e.g., at least 80%, 90%, 95%, or at least 99%, identity to SEQ ID NO: 27 can be utilized.

Tumor-Targeting Drug Delivery Nanoparticles (Nano-Tropins)

Provided herein are novel bifunctional fusion nanoparticles for targeting pharmaceutical agents to pathological areas. The fusion nanoparticles described herein include two or more portions: (i) at least one fusion polymer that includes a sequence that binds to the Exposed Collagenous (XC-) proteins, and an amphiphilic polymer with distinct hydrophobic and hydrophilic domains that can self-assemble with similar polymers to assemble a core-shell structure and (ii) a nanoparticle (e.g., a micelle or liposome) that non-covalently sequesters chemotherapeutic or biologic agents (e.g., FIG. 14A), for example agents with hydrophobic or hydrophilic characteristics or nucleic acids (e.g., FIGS. 14B & 14C). These fusion polymers can also include (iii) linker segments and/or (iv) flanking sequences to improve the functionality, pharmacokinetics, stability, and/or pharmacodynamics of the targeted drug delivery. These fusion nanoparticles may enable tumor-targeted delivery of the chemotherapeutic and biologic agents, e.g., anticancer agents, and may be particularly suited for the transport of drugs with low solubility.

In some embodiments, the drug-binding properties of these fusion nanoparticles are based on the non-covalent sequestering of the drug inside a nanoparticle such as, but not limited to, a micelle or liposome. These nanoparticles can be made of amphiphilic polymers that form a core-shell structure that is useful as a carrier for delivery of drugs as well as nucleic acids. These nanoparticles represent a versatile platform for cancer drug delivery due to their small size (10-100 nm), in vivo stability, prolonged blood circulation times, ability to transport insoluble-drugs, and ability to transport drugs without substantially altering the chemical composition or commercial manufacturing of the drug.

The fusion nanoparticles described herein can include at least one fusion polymer comprising (i) a collagen-binding domain and (ii) an amphiphilic polymer with distinct hydrophobic and hydrophilic block domains that self-assembles with similar polymers to assemble a core-shell structure. In some embodiments of the fusion nanoparticles described herein, the at least one fusion polymer is at least or about 10% (e.g., at least or about 10%, 15%, 20%, 30%, 40%, 50%, 60%, 70%, 80%, or at least or about 90%) of the total number of polymers that comprise the micelle. In some embodiments, the at least one fusion polymer is between about 10% and 50% of the total number of polymers that comprise the micelle.

In some embodiments, the tumor-targeting drug-delivery fusion nanoparticles can further include one or more linkers/spacers, to reduce the steric hindrances between the functional domains. The fusion nanoparticles can have one or more linkers comprising an amino acid sequence selected from the group consisting of SEQ ID NO: 22, SEQ ID NO: 7, SEQ ID NO: 23, SEQ ID NO: 17, SEQ ID NO: 24, SEQ ID NO: 25, SEQ ID NO: 31, SEQ ID NO: 26, and SEQ ID NO: 9. In some embodiments, the fusion polymers are acetylated, amidated and/or PEGylated at N- or C-terminus. Inclusion of D-amino acids, acetylation, amidation, and/or PEGylation may increase the stability of the fusion polymers and make them more resistant to proteolysis.

In some embodiments, the fusion nanoparticles function in the delivery of drugs including but not limited to hydrophobic drugs, hydrophilic drugs, and nucleic acids. In some embodiments, these drugs are Taxanes (e.g., Docetaxel, Paclitaxel), Doxorubicin, epirubicin, Platinum Drugs (Cisplatin, CDDP, DACHPt), R547 (a cyclin-dependent kinase inhibitor), TGX-221 (PI-3 kinase inhibitor), Captothecin, Gemcitabine, 5-fluouracil, Rifampicin, Tamoxifen, Ellipticin, ethotrexate, Daunomycin, estrogen, Curcumin, and various therapeutic siRNAs (see Jhaveri and Torchilin, *Multifunctional polymeric micelles for delivery of drugs and siRNA* April 2014. Frontiers in Pharma. Vol 5. Art 77; Bennet and Kim, *Polymer Nanoparticles for Smart Drug Delivery* 2014. Application of Nano. In Drug Delivery Ch 8 pages 257-310; and Kim et al., *Engineered Polymers for*

*Advanced Drug Delivery March* 2009. Eur J Pharm Biopharm. 71(3):420-430. which are incorporated herein in their entirety).

Generation of the Bifunctional Fusion Polymers

A fusion polymer described herein can be produced by expression of a recombinant nucleic acid encoding the polymer or by chemical synthesis (e.g., by solid-phase synthesis or other methods well known in the art, including synthesis with an ABI peptide synthesizer; Applied Biosystems, Foster City, Calif.). For example, a fusion polymer can be produced by expression of a nucleic acid encoding the protein in prokaryotes. These include but are not limited to microorganisms such as bacteria transformed with recombinant bacteriophage DNA, plasmid DNA or cosmid DNA expression vectors encoding a fusion protein of the invention. The constructs can be expressed in *E. coli* in large scale for in vitro assays. Purification from bacteria is simplified when the sequences include tags for one-step purification by nickel-chelate chromatography. The construct can also contain a tag to simplify isolation of the fusion polymer. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion polymer described herein can also be engineered to contain a cleavage site to aid in protein recovery. Alternatively, the fusion polymers described herein can be expressed directly in a desired host cell for assays in situ.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polymer of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38.

For long-term, high-yield production of recombinant proteins, stable expression can be used. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in $tk^-$, $hgprt^-$ or $aprt^-$ cells respectively. Also, antimetabolite resistance can be used as the basis of selection for dhfr, which confers resistance to methotrexate (Wigler, et al., Proc. Natl. Acad. Sci USA, 77:3567, 1980; O'Hare, et al, Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

Techniques for the isolation and purification of either microbially or eukaryotically expressed polymers of the invention may be by any conventional means such as, for example, preparative chromatographic separations and immunological separations such as those involving the use of monoclonal or polyclonal antibodies or antigen.

Generation of the Tumor-Targeted Drug-Delivery Nanoparticles

Fusion-polymers described herein for construction of a tumor-targeted drug-delivery nanoparticle can be produced by the covalent linkage of a tumor targeting polypeptide to a maleimide-activated polymer with distinct hydrophobic and hydrophilic block domains. The tumor targeting polypeptide, di- or multi-block polymer, and maleimide-activated di-block copolymer can separately be produced by expression of a recombinant nucleic acid encoding the polymer or by chemical synthesis as described above. The tumor targeting aptamer sequence can further comprise one or more linkers. These linkers can be separately produced by expression of a recombinant nucleic acid encoding the polymer or by chemical synthesis or can be expressed with the recombinant polymer, as described previously. One of the one or more linkers can be attached on the N- or C-terminal end of the aptamer and further comprise a cysteine residue such that the cysteine residue is the terminal residue. The di- or multi-block polymer can be produced to similarly comprise one or more linkers. One of the one or more linkers of the polymer can be linked to the end of the polymer that is adjacent to the hydrophilic block and can connect a maleimide-group to the polymer to create the maleimide-activated polymer. This maleimide-group can react with the thiol group of the cysteine residue on the tumor-targeting peptide to site—specifically form a covalent bond between the tumor targeting aptamer and the polymer. The covalent linkage of the tumor-targeting peptide and the di- or multi-block polymer creates a fusion polymer. This fusion polymer can comprise the tumor-targeting domain, one or more linkers, the hydrophilic and hydrophobic blocks in such a structure as to have the propensity to assemble into a hydrophilic shell surrounding a hydrophobic core or bilayer as described herein. The linking of the tumor-targeting peptide to the di- or multi-block polymer is such that when the nanoparticle is assembled, the tumor-targeting domain of the fusion polymer extends outwardly from the hydrophilic surface of the nanoparticle such that the tumor-targeting domain can bind to XC proteins while associated with the nanoparticle.

Methods of Use of the Bifunctional Fusion Polymers and Nanoparticles

The fusion polymers and pharmaceutical compositions described herein can be useful for the treatment of a disease, for example, cancer. The cancer can be, e.g., a primary or metastatic cancer, including but not restricted to, colorectal cancer, breast cancer, brain tumors, non-small cell lung cancer, pancreatic cancer, prostate cancer, sarcoma, carcinoma, and/or melanoma. The cancer can be, e.g., cancer of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and/or throat; sarcoma, or choriocarcinoma. In general, the methods of treating cancer can include administering to a subject having cancer an amount of the fusion polymer or pharmaceutical composition sufficient to treat cancer in the patient. An exemplary method of treating cancer in a subject using the fusion polymers can include: (a) providing an anti-cancer agent; (b) providing a bifunctional fusion polymer that includes: (i) sequences that bind to the anti-cancer agent, and (ii) sequences that bind to the exposed collagens present in cancerous lesions; (c) mixing the anti-cancer agent with the bifunctional fusion polymer at a specific ratio under desired conditions for a sufficiently long period to allow association of the fusion polymer with the anti-cancer agent, thereby forming an anticancer agent/fusion polymer complex; and (d) administering to a subject in need of treatment an effective amount of a pharmaceutical composition comprising the anticancer agent/fusion polymer complex. The conditions for the mixing step can be optimized based on (i) the solubility and stability of the anticancer agent, (ii) the solubility and stability of the fusion polymer, (iii) the N-terminal and C-terminal modifications of the fusion polymers. For example, the mixing step can be performed in phosphate buffered saline (PBS) at 30° C. for 30 min. In some embodiments, the subject is a human. In some embodiments, the cancer is a solid tumor, for example, a sarcoma, a carcinoma, or a melanoma.

An exemplary method of treating cancer in a subject using the fusion nanoparticles can include: (a) providing an anti-cancer agent; (b) providing a bifunctional fusion nanoparticle that can sequester the anti-cancer agent and that comprises at least one bifunctional fusion polymer that can bind to the exposed collagens present in cancerous lesions; (c) mixing the anti-cancer agent with the bifunctional fusion nanoparticle at a specific ratio under desired conditions for a sufficiently long period to allow association of the fusion nanoparticle with the anti-cancer agent, thereby forming an anticancer agent/fusion nanoparticle complex; and (d) administering to a subject in need of treatment an effective amount of a pharmaceutical composition comprising the anticancer agent/fusion nanoparticle complex. The conditions for the mixing step can be optimized based on (i) the solubility and stability of the anticancer agent, (ii) the solubility and stability of the fusion nanoparticle, and (iii) the N-terminal and C-terminal modifications of the fusion polymers (see Kim et al., 2009, Eur J. Pharm Biopharm, 71:420-430; Sutton et al., 2007; Lee et al., 2006; Du and O'Reilly, 2009, Royal Soc Chem, Soft Matter 5:3544-3561; Huertas et al., 2010, Int J. Pharmaceutics, 385:113-142; Hu et al., 2014, Royal Soc Chem. DOI: 10.1039/c3nr05444f; Bennet and Kim, 201, Intech. http://dx.doi.org/10.5772/58422 which are incorporated herein in their entirety). In some embodiments, the subject is a human. In some embodiments, the cancer is a solid tumor, for example, a sarcoma, a carcinoma, or a melanoma.

The fusion polymers and nanoparticles described herein can also be used, e.g., for imaging and/or tracking primary and/or metastatic tumors in a subject. For example, the fusion polymers and nanoparticles can be labeled with a detectable moiety, such as a radioactive isotope, a magnetic compound, an x-ray absorber, a fluorescent molecule, a chemical compound, and/or a biological tag. After administering the labeled fusion polymer or nanoparticle to a subject, the fusion polymers and nanoparticles are targeted to the primary and metastatic tumors in the subject through its collagen binding domain. Tumors can then be detected using computed tomography, radiography, magnetic resonance imaging, laser scanning microscopy, immunohistochemistry, fluorescent microscopy, Raman spectroscopy, optical coherence tomography (OCT), detection of radiation (e.g., x-ray) scattering or absorption, ultrasound, and/or isotope detection. Practitioners will appreciate that determining the dose to be administered to the subject for imaging or tracking is within the skill of the practitioner and will depend upon the type and location of the tumor(s) in the patient, the type of detectable moiety to be used, and the type of imaging to be performed.

Pharmaceutical Compositions, Dosage Regimen, and Methods of Administration

Provided herein are also pharmaceutical compositions comprising one or more of the fusion polymers or nanoparticles described herein. The compositions can further include one or more therapeutic and/or biologic agents known in the art to be effective in treating cancer, i.e., an anti-cancer agent. Such pharmaceutical compositions can be used to treat cancer as described above. In some embodiments, the pharmaceutical composition is administered to a subject in need of treatment intravenously or subcutaneously.

The active ingredient of a pharmaceutical composition can be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. A pharmaceutical composition provided herein can include another delivery agent and a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Certain tumors may be accessible by administration by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the therapeutic compounds can be prepared with carriers that will protect the therapeutic compounds against rapid elimination from the body, such as a controlled release formulation, including implants and microencapsulated delivery systems.

In some embodiments, the pharmaceutical composition can be directly administered to the areas of active angiogenesis. In some embodiments, the pharmaceutical composition can be administered through conventional routes, e.g., intravenously. Microencapsulation technology or liposomes can be used to protect the pharmaceutical compositions during circulation and release them at the site of active angiogenesis.

The pharmaceutical compositions can be included in a container, pack, or dispenser together with instructions for administration.

The therapeutic and/or biologic agents can be administered in an effective amount, at dosages and for periods of time necessary to achieve the desired result. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

Also provided are kits that include one or more of the fusion polymers described herein. Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the fusion polymers described herein, and at least one (e.g., one, two, three, four, five, or more) other composition in a separate vial containing a therapeutic or biologic agent known in the art to be effective in treating cancer.

Compositions and kits as provided herein can be used in accordance with any of the methods (e.g., treatment methods) described above. For example, compositions and kits can be used to treat cancer. Those skilled in the art will be aware of other suitable uses for compositions and kits provided herein, and will be able to employ the compositions and kits for such uses.

EXAMPLES

The invention is further described in the following examples, which do not limit the scope of the invention described in the claims.

Example 1. Optimization and Analysis of Collagen-Binding Sequences

Figures 3A, 3B, 3C, 3D:
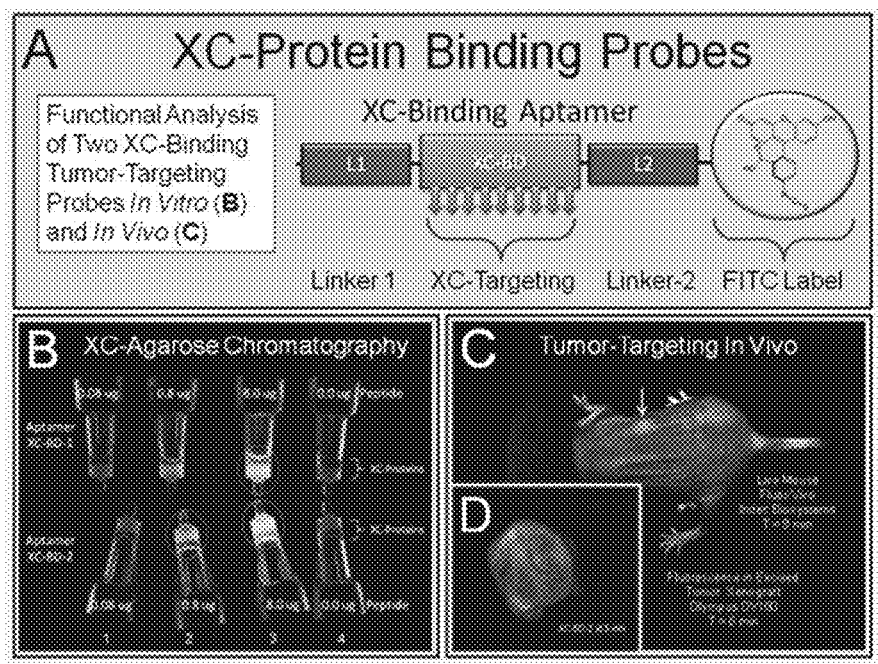
FIG. 3A is a diagram that illustrates the FITC-labeled collagen-binding constructs.
FIG. 3B is an image that shows the collagen-agarose chromatography results of selected FITC-labeled collagen-binding constructs.
FIG. 3C is a nondestructive image that shows fluorescence (arrow) of a subcutaneous tumor in a nude mice intravenously injected with a FITC-labeled collagen-binding construct.
FIG. 3D is an image showing fluorescence of a subcutaneous tumor from a nude mice intravenously injected with a FITC-labeled collagen-binding construct.

Three fluorescein isothiocyanate (FITC)-labeled collagen-binding constructs were generated and tested. Construct 1 (ac-L1/XC-BD1/L3/FITC) had the sequence of Ac-R-R-G-V-H-V-G-W-R-E-P-S-F-M-A-L-S-M-P-H-G-G-S-G-K-(FITC) (SEQ ID NO: 45); Construct 2(ac-L1/XC-BD2/L3/FITC) had the sequence of Ac-R-R-G-V-H-V-G-W-R-E-P-G-R-M-E-L-N-M-P-H-G-G-S-G-K-(FITC) (SEQ ID NO: 46); Construct 3 (ac-L2/XC-BD2/L3/FITC) had the sequence of Ac-R-R-G-V-R-V-A-W-R-E-P-G-R-M-E-L-N-M-P-H-G-G-S-G-K-(FITC) (SEQ ID NO: 47). As shown in FIG. 3A, strategic modifications were made in the collagen-binding domains (XC-BD), the flanking domains, and the respective linkers. Increasing amounts of these constructs were applied to the chromatography columns of Collagen-Agarose beads, followed by successive washes with (1) PBS, (2) PBS/PBS, Tween-20, BSA. The retention of the constructs to the column was documented by use of a blue-light transilluminator with an amber filter; quantitative data was obtained with a Quantus fluorometer. FIG. 3B shows that both Construct 1 and Construct 2 bound to collagen in a dose dependent manner in vitro and were selected for further characterization in vivo. FIGS. 3C-3D show that Construct 2 was efficiently targeted to subcutaneous tumors following intravenous infusion into the tail vein of nude mice.

Example 2. Generation and Test of Tumor-Targeting and Paclitaxel-Binding Fusion Polymers (Taxol-Tropins)

Figure 4A:
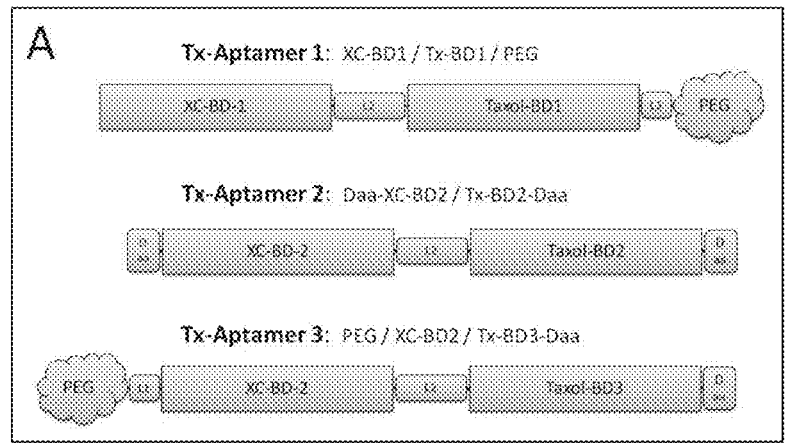
FIG. 4A is a diagram showing the structures of three Taxol-Tropin aptamers (Tx-Aptamers).

Three tumor-targeting and paclitaxel-binding fusion polymers (Taxol-Apatmers or Tx-Apt) were generated and tested. Tx-Apt1 (XC-BD1/TxBD1/PEG) had the sequence of Ac-R-R-G-V-H-V-G-W-R-E-P-S-F-M-A-L-S-M-P-H-G-G-S-G-R-G-V-G-I-M-K-A-C-G-R-T-R-V-T-S-A-G-S-G-(mPEG) (SEQ ID NO: 48). Tx-Apt2 (Daa-XC-BD2/TxBD2-Daa, lower case letters are D-isomers) had the sequence of Ac-[r-r-G-V-H-V-G]-W-R-E-P-G-R-M-E-L-N-M-P-H-[G-G-S-G]-R-G-V-G-I-M-K-A-C-G-R-T-R-H-T-V-R-m-G (SEQ ID NO: 49). Tx-Apt3 (PEG/XC-BD2/TxBD3-Daa, lower case letters are D-isomers) had the sequence of mPEG-K-G-R-R-G-V-H-V-G-W-R-E-P-G-R-M-E-L-N-M-P-H-G-G-S-G-R-G-V-G-I-M-R-A-C-G-R-T-R-H-T-V-R-m-G (SEQ ID NO: 50). The structures of three Tx-Apts were shown diagrammatically in FIG. 4A.

Figure 4B:
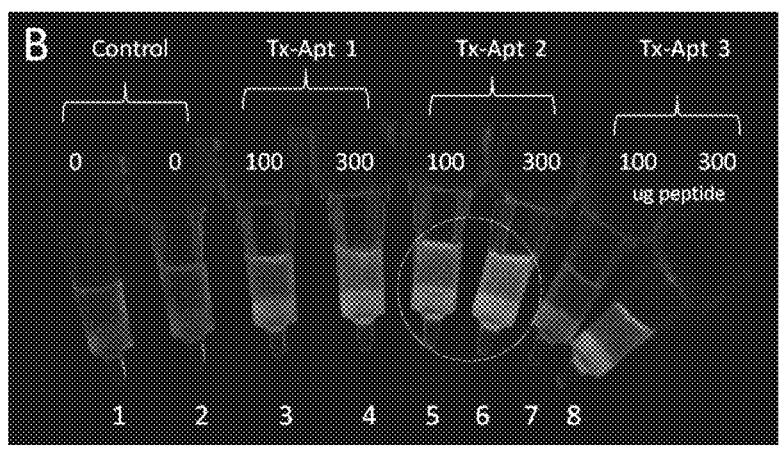
FIG. 4B is an image that shows the collagen-agarose column chromatography results of these Tx-Aptamers.
Figure 4C:
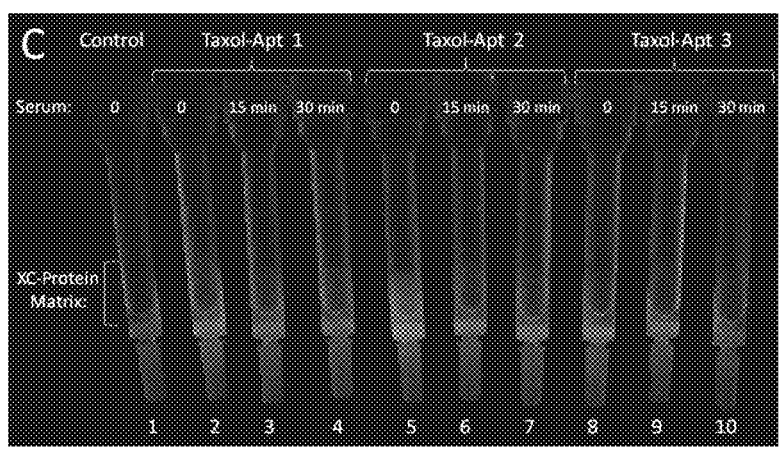
FIG. 4C is an image that shows the comparative serum stability (resistance to proteolysis) of these Tx-Aptamerss.

The Tx-Apts was tested by collagen-agarose column chromatography. Either 100 ug or 300 ug of these Tx-Apts and Oregon Green-488-labeled paclitaxel were applied to the chromatography columns of collagen-agarose beads, followed by successive washes with (1) PBS, (2) PBS/PBS, Tween-20, BSA. The retention of the constructs to the column was documented by use of a blue-light transilluminator with an amber filter; quantitative data was obtained with a Quantus fluorometer. FIG. 4B shows all three Tx-Apts successfully delivered Oregon Green-488-labeled paclitaxel to collagen, and the Tx-Apt2 achieved the best delivery of paclitaxel. Without Tx-Apt, the Oregon Green-488-labeled paclitaxel alone did not bind to collagen (Control), illustrating Tx-Apt-dependent paclitaxel binding to collagen (FIG. 4B). The serum stability (resistance to proteolysis) of these Tx-Apts over time was shown in FIG. 4C, Tx-Apt2 was the most stable of the three Tx-Apts.

Figures 5A, 5B:
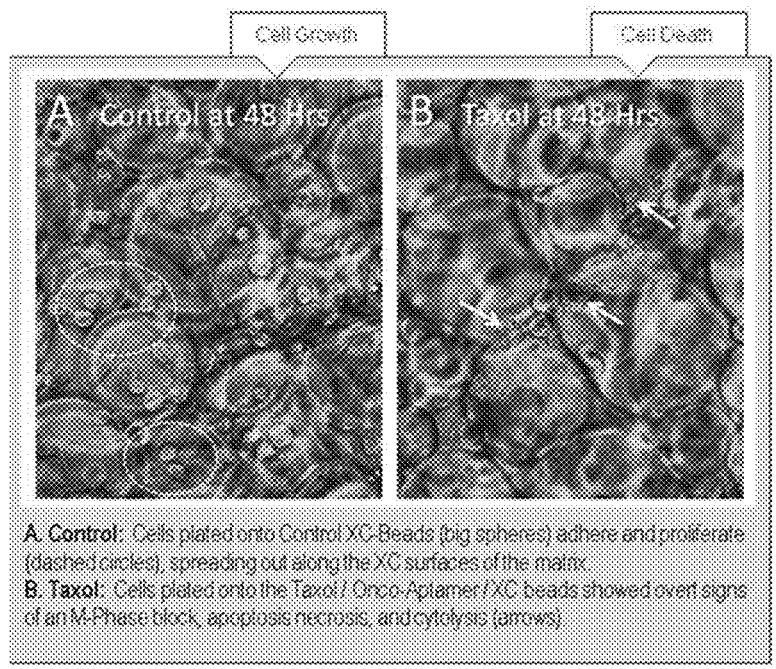
FIG. 5A is an image that shows that MDA-MB-231 breast cancer cells on Control collagen beads readily adhere and proliferate (dashed circles), spreading out along the XC surfaces of the bead matrix at 48 and 72 hours.
FIG. 5B is an image that shows that the fusion XC-binding/Taxol-binding complexes are biologically active: MDA-MB-231 breast cancer cells on Taxol-Aptamer beads showed the classical signs of cell death and destruction, that is, a mitotic block followed by apoptosis, necrosis, and cytolysis (arrows).
Figure 5C:
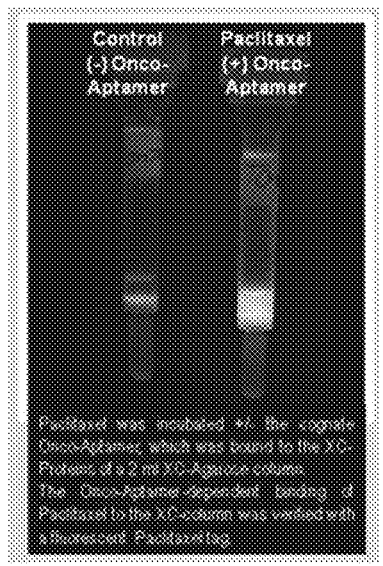
FIG. 5C is an image that shows collagen-agarose column chromatography of control and Taxol-Aptamers, which were used in the cell cultures.

Taxol-aptamers were tested for biological activity in cancer cells in vitro. Collagen-agarose column chromatography was first used to verify that the binding of Taxol to collagen beads was indeed peptide-dependent (FIG. 5C). Human MDA-MB-231 breast cancer cells were plated onto the washed Control and Taxol-Aptamer beads and incubated for one day. The MDA-MB-231 breast cancer cells on Taxol-Aptamer beads showed the classical signs of cell death and destruction, that is, a mitotic block followed by apoptosis, necrosis, and cytolysis (FIG. 5B, arrows). The MDA-MB-231 breast cancer cells on Control collagen beads readily adhered and proliferated (FIG. 5A, dashed circles), spreading out along the XC surfaces of the bead matrix at 48 and 72 hours. Thus, the paclitaxel/Taxol-Aptamer complex was cytotoxic to MDA-MB-231 breast cancer cells when bound to XC protein matrix, indicating retention of the biologic activity of paclitaxel.

Targeting of paclitaxel by Taxol-aptamers to tumor was examined in vivo. Nude mice bearing subcutaneous human pancreatic cancer xenografts were intravenously injected with fluorescent Oregon Green-488 paclitaxel in the presence or absence of the Taxol-aptamers (FIG. 6A). The xenograft tumors were excised and analyzed by fluorescence imaging, which showed the Taxol-aptamer-dependent tumor targeting of paclitaxel (FIG. 6B). Moreover, when used with Taxol-aptamer, paclitaxel exhibited anti-angiogenic activity (i.e., potential efficacy) at 0.2 mg/kg, only $\frac{1}{50}^{th}$ of the normal effective dose of paclitaxel in mice (10 mg/kg) (FIG. 6C). The anti-angiogenic activity seen in targeted paclitaxel treated mice is $\frac{1}{10}$th of the low "metronomic" doses commonly used. These data show Oregon Green-labeled paclitaxel was targeted/delivered to subcutaneous tumors in nude mice in a Taxol-aptamer dependent manner.

The specificity of the Taxol-Tropins for XC-proteins was further demonstrated in vitro utilizing tumor-targeting taxol-binding Tx-Aptamer 2 (see FIG. 4A) and Taxol-Green (see FIG. 16A and FIG. 16B). A tri-layered matrix of Sepharose/XC-Agarose/Sepharose (0.5 ml each) and a control column of 1.5 ml Sepharose 4B (agarose-blank) were prepared. A mixture of fluorescent Taxol-Green (5 ug) and Tx-Aptamer 2 (250 ug) in 1 ml PBS was incubated for 30 minutes at room temperature before being applied to the PBS-equilibrated column. A control mixture contained Taxol-Green minus Tx-Aptamer 2. After application of the Taxol-green mixtures, the columns were washed consecutively with PBS, followed by PBS-T (0.05% Tween-20), followed by 0.5 M NaCl in PBST, followed by 1.0 M PBST. Photos of the resulting columns were obtained under bright field lighting (see FIG. 16A) and blue-light/amber filter (see FIG. 16B).

In this example the column washes represent the systemic circulation, the Sepharose-blanks represent normal (non-diseased) tissues, and the XC-Agarose represents tumor tissues. The bright band seen under the blue light in the XC-agarose and not in the control column is a graphic demonstration of XC-protein selectivity (see FIG. 16B), i.e., a simulation of tumor targeting in vitro. Additionally the Tx-Aptamer 2/Taxol Green fusion complex remained tightly bound to the XC-protein matrix after stringent washing, demonstrating the affinity of the Taxol-Tropin complexes for XC-proteins.

Example 3. Generation and Test of Tumor-Targeting and mAb-Binding Fusion Polymers (mAb-Tropins)

Figure 7A:
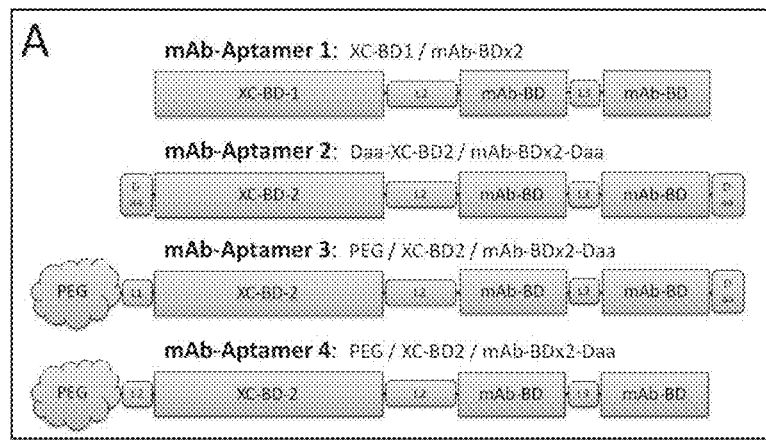
FIG. 7A is a diagram showing the structures of four mAb-Binding, collagen-binding fusion peptides that were generated and tested.
Figure 7B:
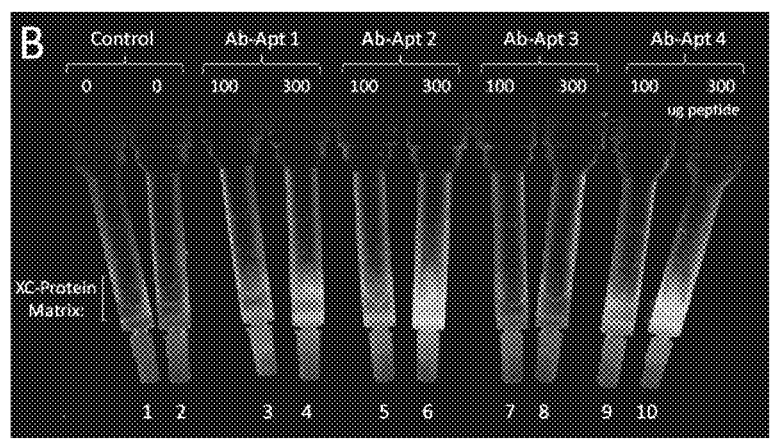
FIG. 7B is an image that shows the collagen-agarose column chromatography results of the four mAb-aptamers from FIG. 7A.
Figure 7C:
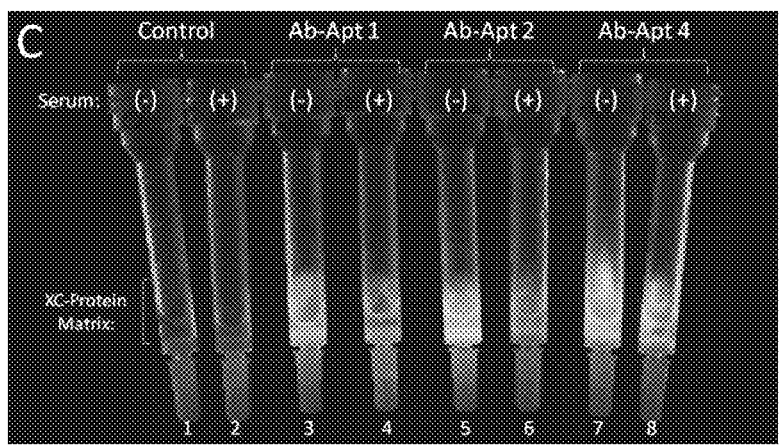
FIG. 7C is an image that shows the serum stability (resistance to proteolysis) of mAb-Aptamer 1, mAb-Aptamer 2 and mAb-Aptamer 4.

FIG. 7A shows the structures of four immunoglobulin-binding, collagen-binding fusion peptides that were generated and tested. The mAb-Aptamer 1 (XC-BD1/mAb-BDx2) had the sequence of R-R-G-V-H-V-G-W-R-E-P-S-F-M-A-L-S-M-P-H-G-G-G-G-G-H-W-R-G-W-V-G-G-G-G-G-H-W-R-G-W-V (SEQ ID NO: 51). The mAb-Aptamer 2 (Daa-XC-BD2/mAb-BDx2-Daa, lower case letters are D-isomers) had the sequence of r-r-G-V-H-V-G-W-R-E-P-G-R-M-E-L-N-M-P-H-G-G-S-G-G-H-W-R-G-W-V-A-G-G-S-G-G-H-W-R-G-W-V-a-a (SEQ ID NO: 52). mAb-Aptamer 3 (PEG/XC-BD2/mAb-BDx2-Daa) had the sequence of (PEG)-C-G-R-R-G-V-H-V-G-W-R-E-P-G-R-M-E-L-N-M-P-H-G-G-S-G-G-H-W-R-G-W-V-A-G-G-S-G-G-H-W-R-G-W-V-a-a (SEQ ID NO: 53). mAb-Aptamer 4 (PEG/XC-BD2/mAb-BDx2-Daa) had the sequence of (PEG)-[C-A-R-R-G-V-H-V-G]-W-R-E-P-G-R-M-E-L-N-M-P-H-[G-G-S-G-G]-H-W-R-G-W-V-A-[G-G-S-G-G]-H-W-R-G-W-V-A-p-t (SEQ ID NO: 54).

The four mAb-aptamers were tested by collagen-agarose column chromatography, which showed mAb-aptamer-dependent antibody (fluorescent Rabbit-Anti-Human Abs) binding to collagen agarose beads (FIG. 7B). Among the four aptamers tested, mAb-Aptamer 2 and mAb-Aptamer 4 resulted higher binding of antibodies to the collagen beads (FIG. 7B). The serum stability (resistance to proteolysis) of mAb-Aptamer 1, mAb-Aptamer 2 and mAb-Aptamer 4 were further analyzed. The PEG-bearing mAb-Aptamer 4 showed the greatest serum stability among the tested mAb-aptamers (FIG. 7C).

Monoclonal antibody bevacizumab (Avastin) was conjugated to a green fluorescent dye 488-Oregon Green, followed by size exclusion chromatography to isolate the labeled Avastin. Structures of two representative mAb-Tropins (M03 and P38) were shown in FIG. 8A. Avastin was incubated with M03 or P38 in PBS for 30 min at 30° C. and then applied to the chromatography column of collagen-agarose beads, followed by successive washes with PBS, and PBS/Tween-20, PBS/Tween-20/BSA. The retention of Avastin to the collagen column was documented by use of a blue-light transilluminator with an amber filter; quantitative data was obtained with a Quantus fluorometer. As shown in FIG. 8B, the combined antibody-binding and collagen-binding activity of M03 was positive and M03-dependent, while that of P38 was nearly negative. Increasing the concentrations of M03 also increased the collagen-bound retentates of Avastin in the column (FIGS. 8BC-8D).

The effect of Avastin/mAb-Tropin on the VEGF-stimulated human vein endothelial cell (HUVEC) proliferation was investigated by passing the culture media through a collagen-agarose chromatography column. Human Vascular Endothelial Cells (HUVEC) were evenly plated in complete growth medium (M200 with 2% serum plus EGF and FGF supplements) and allowed for attachment, growth and division. The cells were then starved in 0.2% serum without supplements for a four-hour period while the chromatography columns were prepared. Avastin/mAb-Tropin complex was loaded onto collagen chromatography column to form VEGF-Trap (XC/mAb-Tropin/Avastin complex) columns. To test whether the collagen-bound Avastin is capable of blocking the VEGF-stimulated HUVEC proliferation, low-serum media was spiked with VEGF (10 ng/ml) and one half of this VEGF-containing medium was poured over either Control columns or our VEGF-Trap (collagen/mAb-Tropin/Avastin complex) columns. The serum-starved cells were then fed with the respective column pass through (eluates). The VEGF-stimulated growth and proliferation of the HUVEC cells were unaffected in the Control columns (FIGS. 9A-C) but were blocked in the VEGF-Trap (collagen/mAb-Tropin/Avastin complex) columns (FIGS. 9D-F). The inhibition of VEGF-stimulated growth by VEGF-Trap columns indicated that Avastin in the collagen-bound/mAB-Tropin/Avastin complexes was biologically active and had anti-angiogenic effects.

Example 4. Generation and Test of Tumor-Targeting and RNA-Binding Fusion Polymers (RNA-Tropins)

FIG. 10A shows the structures of two RNA-binding and collagen-binding fusion peptides that were generated and tested. The RNA-Apt 07 (CPP-R9/XC-BD1) had the sequence of SEQ ID NO: 55. The RNA-Apt 08 (XC-BD1/CPP-R9) had the sequence of SEQ ID NO: 35.

Short oligonucleotides labeled with Oregon Green 488 were incubated with increasing amounts of RNA-Apt 07 or RNA-Apt 08 in PBS for 30 min at 30° C. and then applied to the chromatography column of collagen-agarose beads, followed by successive washes with (1) PBS, (2) PBS/PBS, Tween-20, BSA. The retention to the column was documented by use of a blue-light transilluminator with an amber filter; quantitative data was obtained with a Quantus fluorometer. Both RNA-Apt 07 and RNA-Apt 08 (with polyarginine R9) depleted fluorescently labeled-oligonucleotides from the eluates (FIG. 10B) while retaining the labeled oligonucleotides on the collagen-agarose mini-columns (FIG. 10C).

Example 5. Test of Tumor-Targeting Polypeptide Delivery of IgGs to Tumors in Mice A murine xenograft model of metastatic cancer was established using subcutaneous tumors composed of pancreatic cancer cells (MIA PaCa). Following the establishment of tumors, the mice were injected i.v. via the tail vein and after 60 minutes they were imaged with bright field and fluorescence settings (see FIGS. 11A-11C).

Mice injected with IgG$^{FITC}$ without the collagen-binding tumor-targeting aptamer demonstrated very little accumulation of IgG$^{FITC}$ in the tumor (See FIG. 11A). Conversely, when the mice were injected with IgG$^{FITC}$ linked to a tumor-targeting aptamer the accumulation of IgG was visible within the tumor (see FIG. 11B). Untreated mice were used to determine the level of background fluorescence (see FIG. 11C for control). The accumulation of IgG$^{FITC}$ within the tumor after i.v. injection is evidence of the ability of the tumor-targeting peptides to deliver the IgG directly to the site of the tumor.

Example 6. Generation and Test of Tumor-Targeting and Human Serum Albumin (HSA)-Binding Fusion Polymers Two maleimide-activated tumor-targeting peptides, Albumin-Aptamer 3 (Mal-PEG2-L1-XCBD2a) and Albumin-Aptamer 4 (aXCBD2-L2-PEG2-Mal) (structures shown in FIG. 2E), were generated and tested for their ability to bind both HSA and an XC-agarose column.

HSA was reduced with 3 molar excess DTT, followed by dialysis or desalting into PBS to remove the remaining DTT. This concentration of DTT selectively reduces Cys-34 of HSA. The two Albumin-Aptamer constructs, Apt-3 or Apt-4, were incubated with the reduced HSA overnight at 4° C. The Albumin-Aptamer constructs were then tested by collagen-agarose (XC) column chromatography (FIG. 12).

The XC-bound Albumin-Aptamer constructs were detected using FITC-labeled goat anti-HSA antibodies. Incubation with labeled goat antibodies was followed by stringent washing (PB ST plus 2M NaCl). The XC-bound Albumin-Aptamer constructs were documented by fluorescence photography, as seen in FIG. 12, using a blue-light transilluminator equipped with an amber filter and a Leica V-LUX1 digital camera.

By selectively reducing the Cys-34 of HSA, the maleimide activated linker successfully bound HSA to the collagen-binding aptamer. In FIG. 12 the binding of Apt-3 (structure shown in FIG. 2E) appears to be stronger than that of Apt-4.

Example 7. Tumor-Targeting, Taxol-Binding, Albumin-Linked Fusion Polymers (TargaTaxel)

A structural schematic of the novel tripartite onco-aptamer, CpBio-MA3TX, named TargaTaxel, is shown in FIG. 13 and is an example using the covalent binding of Albumin for protection and shielding of the peptide. This schematic diagrams the (i) maleimide-activated, HSA$^{Cys-34}$ binding domain, (ii) the tumor-targeting domain consisting of a high-performance XC-binding domain, and (iii) an optimized paclitaxel-binding domain for the carrying of taxol. The tethering of HSA to this taxol-binding and tumor-targeting fusion aptamer serves as a "shield" that resists proteolytic degradation by serum proteases. The stable linkage to albumin additionally serves to reduce filtration of the targeting aptamer by the kidneys, thus extending the biological half-life and circulating time of the construct.

This increase in stability and circulating half-life of the constructs can be addressed by the addition of a maleimide group to the N-terminus or C-terminus to link covalently with albumin via HSA Cys-34 or by the addition of a PEG moiety to the N-terminus or C-terminus, among others. These modifications serve to "shield" the constructs and permit a longer biological half-life. Skilled practitioners will appreciate that variations in these constructs are possible and such variants may be useful in the present invention.

Example 8. Generation and Test of Tumor-targeting Nanoparticles

Nanoparticles are useful for in vivo drug delivery due to a long circulating half-life and their ability to improve the solubility, pharmacokinetics, and resulting efficacy of their cargos, particularly hydrophobic agents. By using the tumor-targeting peptide of the present invention linked to a drug-delivering nanoparticle, drugs can be delivered selectively and efficiently to tumors, without substantially altering the chemical composition or manufacturing of the drug.

Schematics of an exemplary nanoparticle tumor-targeting system are shown in FIG. 14A-14C. FIG. 14A is the structure of the maleimide-activated di-block copolymer and a schematic of a bifunctional polymer formed by the linking of a tumor-targeted collagen-binding aptamer and a maleimide-activated di-block copolymer. The maleimide-activated di-block copolymer includes a hydrophobic PDLLA block, a hydrophilic PEG block and a maleimide group connected to the di-block by a linker. The tumor targeting aptamer schematic diagrams a protective D-amino acid cap on the C-terminal for protease resistance, a XC-binding tumor targeting peptide sequence, and a linker at the N-terminus connecting a terminal cysteine residue. The free-cysteine residue enables site-specific covalent coupling to the activated maleimide link on the di-block copolymer creating a fusion polymer. This polymer is incorporated at a ratio of at least or about ~10% (at least or about 10%, 20%, 30%, 40%, 50%, 70%, 90%, or 99%) of the total copolymers that assemble into the micelle nanoparticle.

A schematic for a drug loaded micelle comprising the di-block polymer is shown in FIG. 14B. FIG. 14C is a schematic of a tumor-targeted drug loaded micelle made with fusion polymers displaying a tumor-targeting aptamer on the surface of a micelle. This tumor-targeting sequence directs the nanoparticle to seek out and accumulate in the diseased/cancerous tissues following intravenous infusion. Thus, the fusion nanoparticles described herein may make conventional chemotherapeutic and biologic agents more efficient with great efficacy while lessening unwanted side effects, improving the overall Therapeutic Index and patient survival.

In vitro testing of the tumor-targeting nanoparticles was performed using XC-agarose chromatography. FIGS. 15A-15C are schematics, images and graphs of a nanoparticle tumor-targeting system using coumarin-6 as a model hydrophobic drug. A schematic of the two tumor-targeted collagen-binding aptamers that were tested is shown in FIG. 15A.

Polymer micelles were prepared in H₂O by a solvent evaporation method using 5% PEG-PDLLA di-block polymers and 0.5% maleimide-activated di-block polymers PEG-PLGA in DCM. Micelles were then filtrated (0.45 u), diluted with PBS (1:1) and coupled overnight to the free cysteine residue on the terminus of the tumor-targeting aptamer (see Kim et al., 2009, Eur J. Pharm Biopharm, 71:420-430; Sutton et al., 2007; Lee et al., 2006; Du and O'Reilly, 2009, Royal Soc Chem, Soft Matter 5:3544-3561; Huertas et al., 2010, Int J. Pharmaceutics, 385:113-142; Hu et al., 2014, Royal Soc Chem. DOI: 10.1039/c3nr05444f; Bennet and Kim, 201, Intech. http://dx.doi.org/10.5772/58422 which are incorporated herein in their entirety). This coupling reaction was performed in PBS for 2-4 hours at room temperature or overnight at 4° C. or room temperature and resulted in the covalent linkage of the copolymer PEG-maleimide group to the targeting aptamer.

The resulting fusion nanoparticles were analyzed by XC-agarose chromatography. FIG. 15B are images of a XC-agarose chromatography analysis of polymeric micelles loaded with Courmarin-6 and coupled to the tumor-targeting aptamers. The fusion nanoparticles exhibited tumor-targeting peptide-dependent binding to the XC-agarose beads under stringent washing conditions (FIG. 15B). Quantification of the column eluates confirmed the tumor-targeting peptide-dependent reduction of Coumarin-6/nanoparticles in the eluates (FIG. 15C). Fusion nanoparticles with tumor-targeting Aptamer 2 exhibited less efficient retention of Coumarin-6 and binding to the XC-agarose beads than Aptamer 1. These data successfully demonstrated the bifunctional tumor-targeting and drug delivery nanoparticle system.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising the amino acid sequence of SEQ ID NO: 49.

2. A pharmaceutical composition comprising the polypeptide of claim 1 and a pharmaceutically acceptable carrier.

3. The polypeptide of claim 1, wherein the polypeptide is acetylated, amidated, and/or further PEGylated.

4. The polypeptide of claim 1, further comprising a thio-reactive maleimide group linked to a terminus of the polypeptide.

5. A composition, comprising the polypeptide of claim 1 bound to a chemotherapeutic agent selected from the group consisting of: paclitaxel, docetaxel, or nab-paclitaxel.

6. A pharmaceutical composition comprising the composition of claim 5 and a pharmaceutically acceptable carrier.

7. The composition of claim 5, wherein the chemotherapeutic agent is paclitaxel.

8. The composition of claim 5, wherein the chemotherapeutic agent is docetaxel.

9. The composition of claim 5, wherein the chemotherapeutic agent is nab-paclitaxel.

10. A polypeptide comprising the amino acid sequence of SEQ ID NO: 50.

11. A pharmaceutical composition comprising the polypeptide of claim 10 and a pharmaceutically acceptable carrier.

12. The polypeptide of claim 10, wherein the polypeptide is acetylated, amidated, and/or further PEGylated.

13. The polypeptide of claim 10, further comprising a thio-reactive maleimide group linked to a terminus of the polypeptide.

14. A composition, comprising the polypeptide of claim 10 bound to a chemotherapeutic agent selected from the group consisting of: paclitaxel, docetaxel, or nab-paclitaxel.

15. A pharmaceutical composition comprising the composition of claim 14 and a pharmaceutically acceptable carrier.

16. The composition of claim 14, wherein the chemotherapeutic agent is paclitaxel.

17. The composition of claim 14, wherein the chemotherapeutic agent is docetaxel.

18. The composition of claim 14, wherein the chemotherapeutic agent is nab-paclitaxel.

* * * * *

SEQUENCE LISTING

```
<160> NUMBER OF SEQ ID NOS: 59

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Arg Glu Pro Ser Phe Met Ala Leu Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Arg Glu Pro Gly Arg Met Glu Leu Asn
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Val Gly Ile Met Lys Ala Cys Gly Arg Thr Arg Val Thr Ser
1               5                   10                  15

<210> SEQ ID NO 4
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gly Val Gly Ile Met Lys Ala Cys Gly Arg Thr Arg His Thr Val
1               5                   10                  15

Arg

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: D-Met

<400> SEQUENCE: 5

Arg Gly Val Gly Ile Met Lys Ala Cys Gly Arg Thr Arg His Thr Val
1               5                   10                  15

Arg Met Gly

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Phe Met Thr Lys Thr Met Glu Cys Gly Arg Thr Arg His Thr Val
1               5                   10                  15

Arg Met Gly

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Ser Gly
1

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Gly Val His Val Gly
1               5
```

-continued

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-Arg

<400> SEQUENCE: 9

Arg Arg Gly Val His Val Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Gly Arg Arg Gly Val His Val Gly
1               5

<210> SEQ ID NO 11
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Arg Gly Val His Val Gly Trp Arg Glu Pro Ser Phe Met Ala Leu
1               5                   10                  15

Ser Met Pro His Gly Gly Ser Gly Arg Gly Val Gly Ile Met Lys Ala
            20                  25                  30

Cys Gly Arg Thr Arg Val Thr Ser Ala Gly Ser Gly
        35                  40

<210> SEQ ID NO 12
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (42)..(42)
<223> OTHER INFORMATION: D-Met

<400> SEQUENCE: 12

Arg Arg Gly Val His Val Gly Trp Arg Glu Pro Gly Arg Met Glu Leu
1               5                   10                  15

Asn Met Pro His Gly Gly Ser Gly Arg Gly Val Gly Ile Met Lys Ala
            20                  25                  30

Cys Gly Arg Thr Arg His Thr Val Arg Met Gly
        35                  40
```

```
<210> SEQ ID NO 13
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (44)..(44)
<223> OTHER INFORMATION: D-Met

<400> SEQUENCE: 13

Lys Gly Arg Arg Gly Val His Val Gly Trp Arg Glu Pro Gly Arg Met
1               5                   10                  15

Glu Leu Asn Met Pro His Gly Gly Ser Gly Arg Gly Val Gly Ile Met
            20                  25                  30

Arg Ala Cys Gly Arg Thr Arg His Thr Val Arg Met Gly
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (44)..(44)
<223> OTHER INFORMATION: D-Pro
<220> FEATURE:
<221> NAME/KEY: MOD_RES
<222> LOCATION: (45)..(45)
<223> OTHER INFORMATION: D-Thr

<400> SEQUENCE: 14

Arg Arg Gly Val His Val Gly Trp Arg Glu Pro Gly Arg Met Glu Leu
1               5                   10                  15

Asn Met Pro His Gly Gly Ser Gly Arg Gly Val Gly Ile Met Lys Ala
            20                  25                  30

Cys Gly Arg Thr Arg His Thr Val Arg Met Gly Pro Thr
        35                  40                  45

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Trp Arg Gly Trp Val
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Gly Gly Gly Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ser Gly Gly
1               5

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Arg Gly Val His Val Gly Trp Arg Glu Pro Ser Phe Met Ala Leu
1               5                   10                  15

Ser Met Pro His Gly Gly Gly Gly His Trp Arg Gly Trp Val Gly
            20                  25                  30

Gly Gly Gly Gly His Trp Arg Gly Trp Val
        35                  40

<210> SEQ ID NO 19
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (44)..(45)
<223> OTHER INFORMATION: D-Ala

<400> SEQUENCE: 19

Arg Arg Gly Val His Val Gly Trp Arg Glu Pro Gly Arg Met Glu Leu
1               5                   10                  15

Asn Met Pro His Gly Gly Ser Gly Gly His Trp Arg Gly Trp Val Ala
            20                  25                  30

Gly Gly Ser Gly Gly His Trp Arg Gly Trp Val Ala Ala
        35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(47)
<223> OTHER INFORMATION: D-Ala
```

<400> SEQUENCE: 20

Cys Gly Arg Arg Gly Val His Val Gly Trp Arg Glu Pro Gly Arg Met
1               5                   10                  15

Glu Leu Asn Met Pro His Gly Gly Ser Gly Gly His Trp Arg Gly Trp
            20                  25                  30

Val Ala Gly Gly Ser Gly Gly His Trp Arg Gly Trp Val Ala Ala
        35                  40                  45

<210> SEQ ID NO 21
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (47)..(47)
<223> OTHER INFORMATION: D-Pro
<220> FEATURE:
<221> NAME/KEY: MOD_RES
<222> LOCATION: (48)..(48)
<223> OTHER INFORMATION: D-Thr

<400> SEQUENCE: 21

Cys Ala Arg Arg Gly Val His Val Gly Trp Arg Glu Pro Gly Arg Met
1               5                   10                  15

Glu Leu Asn Met Pro His Gly Gly Ser Gly Gly His Trp Arg Gly Trp
            20                  25                  30

Val Ala Gly Gly Ser Gly Gly His Trp Arg Gly Trp Val Ala Pro Thr
        35                  40                  45

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly
1

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Gly Ser Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Ser Gly Ser Gly Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Gly Gly Ser Lys
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Gly Gly Ser Gly Gly Ser Gly
1               5

<210> SEQ ID NO 27
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: MiniPEG-Ser
<220> FEATURE:
<221> NAME/KEY: MOD_RES
<222> LOCATION: (48)..(48)
<223> OTHER INFORMATION: D-Met
<220> FEATURE:
<221> NAME/KEY: MOD_RES
<222> LOCATION: (50)..(50)
<223> OTHER INFORMATION: D-Ser

<400> SEQUENCE: 27

Ser Gly Gly Ser Gly Ala Arg Arg Gly Val His Val Gly Trp Arg Glu
1               5                   10                  15

Pro Gly Arg Met Glu Leu Asn Met Pro His Gly Gly Ser Gly Arg Gly
            20                  25                  30

Val Gly Ile Met Lys Ala Cys Gly Arg Thr Arg His Thr Val Arg Met
        35                  40                  45

Gly Ser
    50

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Acetyl-D-Ala
<220> FEATURE:
```

```
<221> NAME/KEY: MOD_RES
<222> LOCATION: (2)..(3)
<223> OTHER INFORMATION: D-Arg

<400> SEQUENCE: 28

Ala Arg Arg Gly Val His Val Gly Trp Arg Glu Pro Gly Arg Met Glu
1               5                   10                  15

Leu Asn Met Pro His Gly Gly Ser Gly Ser Gly Gly Ser Gly Cys
                20                  25                  30

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Arg Arg Arg Arg Arg Arg Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-Arg

<400> SEQUENCE: 30

Arg Arg Arg Arg Arg Arg Arg Arg Arg
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ser Gly Gly Ser Gly Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Arg Arg Gly Val His Val Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 33

Cys Gly Ser Gly Gly
1               5

<210> SEQ ID NO 34
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly
1

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Arg Arg Gly Val His Val Gly Trp Arg Glu Pro Ser Phe Met Ala Leu
1               5                   10                  15

Ser Met Pro His Gly Gly Arg Arg Arg Arg Arg Arg Arg Arg Arg
            20                  25                  30

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(39)
<223> OTHER INFORMATION: D-Arg

<400> SEQUENCE: 36

Cys Ala Arg Arg Gly Val His Val Gly Trp Arg Glu Pro Gly Arg Met
1               5                   10                  15

Glu Leu Asn Met Pro His Gly Gly Ser Gly Gly Ser Gly Gly Arg Arg
            20                  25                  30

Arg Arg Arg Arg Arg Arg Arg
                35

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(9)
<223> OTHER INFORMATION: D-Arg
<220> FEATURE:
<221> NAME/KEY: MOD_RES
<222> LOCATION: (33)..(33)
<223> OTHER INFORMATION: D-Gln
<220> FEATURE:
```

```
<221> NAME/KEY: MOD_RES
<222> LOCATION: (34)..(34)
<223> OTHER INFORMATION: D-Pro
<220> FEATURE:
<221> NAME/KEY: MOD_RES
<222> LOCATION: (35)..(35)
<223> OTHER INFORMATION: D-Thr

<400> SEQUENCE: 37

Arg Arg Arg Arg Arg Arg Arg Arg Arg Gly Gly Arg Gly Val His
1               5                   10                  15

Val Gly Trp Arg Glu Pro Gly Arg Met Glu Leu Asn Met Pro His Gly
            20                  25                  30

Gln Pro Thr
        35

<210> SEQ ID NO 38
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(14)
<223> OTHER INFORMATION: D-Arg
<220> FEATURE:
<221> NAME/KEY: MOD_RES
<222> LOCATION: (38)..(38)
<223> OTHER INFORMATION: D-Gln
<220> FEATURE:
<221> NAME/KEY: MOD_RES
<222> LOCATION: (39)..(39)
<223> OTHER INFORMATION: D-Pro
<220> FEATURE:
<221> NAME/KEY: MOD_RES
<222> LOCATION: (40)..(40)
<223> OTHER INFORMATION: D-Thr

<400> SEQUENCE: 38

Cys Gly Ser Gly Gly Arg Arg Arg Arg Arg Arg Arg Arg Gly Gly
1               5                   10                  15

Arg Arg Gly Val His Val Gly Trp Arg Glu Pro Gly Arg Met Glu Leu
            20                  25                  30

Asn Met Pro His Gly Gln Pro Thr
            35                  40

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Arg Ser Phe Cys Thr Asp Trp Pro Ala His Lys Ser Cys Lys Pro
1               5                   10                  15

Leu

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 40

Arg Gln Met Glu Asp Ile Cys Leu Pro Arg Trp Gly Cys Leu Trp Gly
1               5                   10                  15

Asp

<210> SEQ ID NO 41
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (46)..(46)
<223> OTHER INFORMATION: D-Arg
<220> FEATURE:
<221> NAME/KEY: MOD_RES
<222> LOCATION: (47)..(47)
<223> OTHER INFORMATION: D-Ala

<400> SEQUENCE: 41

Arg Arg Gly Val His Val Gly Trp Arg Glu Pro Gly Arg Met Glu Leu
1               5                   10                  15

Asn Met Pro His Gly Gly Ser Gly Gly Ser Gly Gly Thr Arg Ser Phe
                20                  25                  30

Cys Thr Asp Trp Pro Ala His Lys Ser Cys Lys Pro Leu Arg Ala
            35                  40                  45

<210> SEQ ID NO 42
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (46)..(46)
<223> OTHER INFORMATION: D-Glu
<220> FEATURE:
<221> NAME/KEY: MOD_RES
<222> LOCATION: (47)..(47)
<223> OTHER INFORMATION: D-Asp

<400> SEQUENCE: 42

Arg Arg Gly Val His Val Gly Trp Arg Glu Pro Gly Arg Met Glu Leu
1               5                   10                  15

Asn Met Pro His Gly Gly Ser Gly Gly Ser Gly Gly Arg Gln Met Glu
                20                  25                  30

Asp Ile Cys Leu Pro Arg Trp Gly Cys Leu Trp Gly Asp Glu Asp
            35                  40                  45

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic

```
              polypeptide
<220> FEATURE:
<221> NAME/KEY: MOD_RES
<222> LOCATION: (1)..(1)
<223> OTHER INFORMATION: Maleimide-PEG2-Ser
<220> FEATURE:
<221> NAME/KEY: MOD_RES
<222> LOCATION: (28)..(28)
<223> OTHER INFORMATION: D-Gln
<220> FEATURE:
<221> NAME/KEY: MOD_RES
<222> LOCATION: (29)..(29)
<223> OTHER INFORMATION: D-Pro
<220> FEATURE:
<221> NAME/KEY: MOD_RES
<222> LOCATION: (30)..(30)
<223> OTHER INFORMATION: D-Thr

<400> SEQUENCE: 43

Ser Gly Gly Ser Gly Ala Arg Arg Gly Val His Val Gly Trp Arg Glu
1               5                   10                  15

Pro Gly Arg Met Glu Leu Asn Met Pro His Gly Gln Pro Thr
            20                  25                  30

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(3)
<223> OTHER INFORMATION: D-Arg
<220> FEATURE:
<221> NAME/KEY: MOD_RES
<222> LOCATION: (28)..(28)
<223> OTHER INFORMATION: Lys-PEG2-Maleimide

<400> SEQUENCE: 44

Ala Arg Arg Gly Val His Val Gly Trp Arg Glu Pro Gly Arg Met Glu
1               5                   10                  15

Leu Asn Met Pro His Gly Gly Ser Gly Gly Ser Lys
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Arg
<220> FEATURE:
<221> NAME/KEY: MOD_RES
<222> LOCATION: (25)..(25)
<223> OTHER INFORMATION: Lys-(FITC)

<400> SEQUENCE: 45

Arg Arg Gly Val His Val Gly Trp Arg Glu Pro Ser Phe Met Ala Leu
1               5                   10                  15

Ser Met Pro His Gly Gly Ser Gly Lys
            20                  25
```

```
<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Arg
<220> FEATURE:
<221> NAME/KEY: MOD_RES
<222> LOCATION: (25)..(25)
<223> OTHER INFORMATION: Lys-(FITC)

<400> SEQUENCE: 46

Arg Arg Gly Val His Val Gly Trp Arg Glu Pro Gly Arg Met Glu Leu
1               5                   10                  15

Asn Met Pro His Gly Gly Ser Gly Lys
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Arg
<220> FEATURE:
<221> NAME/KEY: MOD_RES
<222> LOCATION: (25)..(25)
<223> OTHER INFORMATION: Lys-(FITC)

<400> SEQUENCE: 47

Arg Arg Gly Val Arg Val Ala Trp Arg Glu Pro Gly Arg Met Glu Leu
1               5                   10                  15

Asn Met Pro His Gly Gly Ser Gly Lys
            20                  25

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-Arg
<220> FEATURE:
<221> NAME/KEY: MOD_RES
<222> LOCATION: (44)..(44)
<223> OTHER INFORMATION: Gly-mPEG

<400> SEQUENCE: 48

Arg Arg Gly Val His Val Gly Trp Arg Glu Pro Ser Phe Met Ala Leu
1               5                   10                  15

Ser Met Pro His Gly Gly Ser Gly Arg Gly Val Gly Ile Met Lys Ala
            20                  25                  30

Cys Gly Arg Thr Arg Val Thr Ser Ala Gly Ser Gly
        35                  40
```

```
<210> SEQ ID NO 49
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (42)..(42)
<223> OTHER INFORMATION: D-Met

<400> SEQUENCE: 49

Arg Arg Gly Val His Val Gly Trp Arg Glu Pro Gly Arg Met Glu Leu
1               5                   10                  15

Asn Met Pro His Gly Gly Ser Gly Arg Gly Val Gly Ile Met Lys Ala
            20                  25                  30

Cys Gly Arg Thr Arg His Thr Val Arg Met Gly
        35                  40

<210> SEQ ID NO 50
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: MPEG-Lys
<220> FEATURE:
<221> NAME/KEY: MOD_RES
<222> LOCATION: (44)..(44)
<223> OTHER INFORMATION: D-Met

<400> SEQUENCE: 50

Lys Gly Arg Arg Gly Val His Val Gly Trp Arg Glu Pro Gly Arg Met
1               5                   10                  15

Glu Leu Asn Met Pro His Gly Gly Ser Gly Arg Gly Val Gly Ile Met
            20                  25                  30

Arg Ala Cys Gly Arg Thr Arg His Thr Val Arg Met Gly
        35                  40                  45

<210> SEQ ID NO 51
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Arg Gly Val His Val Gly Trp Arg Glu Pro Ser Phe Met Ala Leu
1               5                   10                  15

Ser Met Pro His Gly Gly Gly Gly His Trp Arg Gly Trp Val Gly
            20                  25                  30

Gly Gly Gly Gly His Trp Arg Gly Trp Val
        35                  40
```

```
<210> SEQ ID NO 52
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: D-Arg
<220> FEATURE:
<221> NAME/KEY: MOD_RES
<222> LOCATION: (44)..(45)
<223> OTHER INFORMATION: D-Ala

<400> SEQUENCE: 52

Arg Arg Gly Val His Val Gly Trp Arg Glu Pro Gly Arg Met Glu Leu
1               5                   10                  15

Asn Met Pro His Gly Gly Ser Gly Gly His Trp Arg Gly Trp Val Ala
            20                  25                  30

Gly Gly Ser Gly Gly His Trp Arg Gly Trp Val Ala Ala
        35                  40                  45

<210> SEQ ID NO 53
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: (PEG)-Cys
<220> FEATURE:
<221> NAME/KEY: MOD_RES
<222> LOCATION: (46)..(47)
<223> OTHER INFORMATION: D-Ala

<400> SEQUENCE: 53

Cys Gly Arg Arg Gly Val His Val Gly Trp Arg Glu Pro Gly Arg Met
1               5                   10                  15

Glu Leu Asn Met Pro His Gly Gly Ser Gly Gly His Trp Arg Gly Trp
            20                  25                  30

Val Ala Gly Gly Ser Gly Gly His Trp Arg Gly Trp Val Ala Ala
        35                  40                  45

<210> SEQ ID NO 54
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: (PEG)-Cys
<220> FEATURE:
<221> NAME/KEY: MOD_RES
<222> LOCATION: (47)..(47)
<223> OTHER INFORMATION: D-Pro
<220> FEATURE:
<221> NAME/KEY: MOD_RES
<222> LOCATION: (48)..(48)
<223> OTHER INFORMATION: D-Thr

<400> SEQUENCE: 54
```

```
Cys Ala Arg Arg Gly Val His Val Gly Trp Arg Glu Pro Gly Arg Met
1               5                   10                  15

Glu Leu Asn Met Pro His Gly Gly Ser Gly Gly His Trp Arg Gly Trp
                20                  25                  30

Val Ala Gly Gly Ser Gly Gly His Trp Arg Gly Trp Val Ala Pro Thr
            35                  40                  45
```

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Arg Arg Arg Arg Arg Arg Arg Arg Arg Arg Gly Val His Val Gly
1               5                   10                  15

Trp Arg Glu Pro Ser Phe Met Ala Leu Ser Met Pro His Gly Gly
                20                  25                  30
```

<210> SEQ ID NO 56
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: D-Gln
<220> FEATURE:
<221> NAME/KEY: MOD_RES
<222> LOCATION: (34)..(34)
<223> OTHER INFORMATION: D-Pro
<220> FEATURE:
<221> NAME/KEY: MOD_RES
<222> LOCATION: (35)..(35)
<223> OTHER INFORMATION: D-Thr-amide

<400> SEQUENCE: 56

```
Cys Gly Ser Gly Gly Ser Gly Gly Ser Gly Ala Arg Arg Gly Val His
1               5                   10                  15

Val Gly Trp Arg Glu Pro Gly Arg Met Glu Leu Asn Met Pro His Gly
                20                  25                  30

Gln Pro Thr
        35
```

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Cys Gly Arg Arg Gly Val His Val Gly
1               5
```

<210> SEQ ID NO 58
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 58

Cys Ala Arg Arg Gly Val His Val Gly
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

His His His His His His
1               5
```